United States Patent [19]
Coquerel et al.

[11] Patent Number: 6,022,409
[45] Date of Patent: Feb. 8, 2000

[54] METHOD OF RESOLUTION OF TWO ENANTIOMERS BY CRYSTALLIZATION

[75] Inventors: Gerard Coquerel, Notre-Dame-de-Bondeville; Marie-Noelle Petit, Mont-Saint-Aignan; Roger Bouaziz, Paris, all of France

[73] Assignee: The University of Rouen, Mont-Saint Aignan, France

[21] Appl. No.: 08/619,477

[22] PCT Filed: Sep. 22, 1994

[86] PCT No.: PCT/FR94/01107

§ 371 Date: Oct. 2, 1996

§ 102(e) Date: Oct. 2, 1996

[87] PCT Pub. No.: WO95/08522

PCT Pub. Date: Mar. 30, 1995

[30] Foreign Application Priority Data

Sep. 23, 1993 [FR] France .................................. 93 11354

[51] Int. Cl.[7] .............................. C30B 7/14; C30B 29/54
[52] U.S. Cl. .............................. 117/68; 117/70; 117/925; 117/926; 117/927; 23/300; 23/311
[58] Field of Search ............................ 117/68, 70, 925, 117/976, 927; 23/300, 391

[56] References Cited

FOREIGN PATENT DOCUMENTS 1456627  9/1966  France .
1197809  7/1970  United Kingdom .

OTHER PUBLICATIONS

G. Coquerel, et al., "optical Resolution of (±) –N–Acylnorfenfluramine Derivatives by Preferential Crystallization", Tetrahedron Letters, vol. 31, No. 15, pp. 2143–21244 (1990).

A. Collet, et al, "Optical Resolution by Direct Crystallization of Enantiomer Mixtures", Chemical Reviews, vol. 80, No. 3, pp. 215–230 (1980).

G. Amiard, "Sur le dédoublement direct de la thréonine, par entrainement", Bulletin De La Societe Chimique De France, No. 81, p. 447, (1956).

Primary Examiner—Robert Kunemund
Attorney, Agent, or Firm—Schnader Harrison Segal & Lewis; Gerard J. Weiser

[57] ABSTRACT

A method of optical enantiomer resolution by preferential crystallization involves entering, each time crystallization starts, the two-phase domain containing excess enantiomer and the saturated solution, and cooling according to a well-defined kinetic schedule. A racemic mixture of fine particle size is added to the mother liquors obtained after harvesting the crystals, the mother liquors then being heated to a temperature lower than that of homogenization of the solution so that excess enantiomer is present only in a solid state in equilibrium with the solution. Further cooling produces the other enantiomer and completes the cycle of operations which may then be carried out repetitively.

19 Claims, 8 Drawing Sheets

METHOD OF RESOLUTION OF TWO ENANTIOMERS BY CRYSTALLIZATION

The present invention concerns the area of separation of two antipodes optical of a species chemical by crystallization preferential. This method rests on crystallization alternate of two compounds chiral designated R and S, by producing a conglomerate in a solvent A and for a range given of temperature $\Delta T$. This means that in this range of temperature any mixture in equilibrium thermodynamic of two antipodes with the solution consists of two types of crystals containing each only molecules of the same configuration, incorporating or not the molecules of solvent (solvates). The existence of such conglomerate without miscibility in the state-solid will be implicitly assumed in that which follows, at least in the range of temperature $\Delta T$ and for the solvent A.

The technique of crystallization preferential is widely employed in laboratories and in the industry owing to the major advantages that it offers:

- it avoids use of an agent chiral intermediate, laborious, whose recovery later implies losses rarely less than 10% (De Min. M., Levy. G., and Michaeu, J. C. (1988) J. Chim. Phys. 85, 603–19).
- the two antipodes are obtained directly, contrary to the method employing resolution classic by formation of salts diastereoisomeric;
- the yield is theoretically quantitative as a result of recyclings successive;
- purification of the crystals of enantiomers crude obtained is easy.

Two classes of factors influence crystallization of antipodes optical, on the one hand, parameters related to equilibrium heterogeneous ternary and on the other hand, factors that intervene in the kinetics of crystallization.

The parameters related to equilibrium heterogeneous ternary comprise:

- the positions of the surfaces of crystallization of species solid that are deposited at each temperature, and more particularly, the values of the solubilities of the phases stable and metastable, of the mixture racemic $s(\pm)$ and the antipodes $s(+)=s(-)$, as a function of the temperature, and the ratio of solubilities $\alpha=s(\pm)/s(+)$;
- the extent of the domains stable and metastable of solutions solid, of racemate, of solvate racemic, of solvate active and varieties polymorphic of the solids crystallized.

The factors intervening in the kinetics of crystallization comprise:

- the factors internal to the crystals in relation to bonds between molecules, which are nonmodifiable by the experimenter;
- the factors external that are modifiable by the experimenter; this involves the nature of the solvent, the nature and the concentration of the impurities, the supersaturation acquired as a function of the time, the range of the temperature $\Delta T$, the rate and the method of agitation, the weight and the particle size of the nuclei, the effect of the wall, etc.

These two classes of factors influence directly the yield, the purity of the phases obtained and the sequence of operations of separation. The feasibility of filtration will be thus dependent on the spectrum particle size and the habit of the crystals, the viscosity of the suspension, the pressure of vapor of the solvent, supersaturations acquired by each of the antipodes and the presence possible of a racemate true with characteristics metastable. These choices can also intervene in the kinetics of racemization of antipodes or degradation of the molecule.

For each aggregate comprising the pair of antipodes (R and S) and solvent (A), the factors intervening on kinetics are a case special.

The present invention seeks to improve the methods for crystallization preferential of the art prior from a better understanding of the equilibria heterogeneous ternary achieved from solvent A and antipodes optical R and S. In effect, knowledge of the equilibrium heterogeneous furnished data exploited in the process of the invention to accomplish resolution more effective and rational of the two antipodes optical by crystallization preferential (or balancing).

More particularly, the process of the invention permits optimization and generalization of a process of the type described in Patent French No. 1 456 627 concerning resolution of acid glutamic and its salts.

SUMMARY OF INVENTION

The process of the invention rests on a modification of the scope general of the processes classic designated below SIPC for "Seeded isothermal prefrential crystallization" and the variants polythermal, owing to the exploitation of the information contained in the representation of the equilibria ternary: antipode R—antipode S—solvent A.

SUMMARY OF INVENTION

The process of the invention consists:

a) of producing an aggregate composed of the mixture racemic of crystals in the form of conglomerate, a first enantiomer and solvent, whose point figurative E, defined by the variables concentration and temperature $T_E$, is situated in the domain two-phase of the first enantiomer in excess, and in equilbrium with its solution saturated;

b) of applying a law of programming of cooling of the temperature to the mixture two-phase prepared in the stage preceding, so that the liquors-mother retain weak supersaturation which favors growth of the enantiomer present in the form of crystals, while preventing nucleation spontaneous of the second enantiomer present in the solution;

c) of adapting during the entire duration of the growth crystalline of the stage preceding a rate of agitation slightly increasing as a function of time so that this is at any moment sufficiently slow to favor growth of the first enantiomer, while avoiding generation of forces of striction too substantial, provoking nucleation uncontrolled, and sufficiently rapid to achieve a suspension homogeneous and a replenishment rapid of the liquor-mother around each crystallite of the first enantiomer;

d) of collecting the crystals of the first enantiomer;

e) of adding to the liquor-mother resulting from collection accomplished in the stage preceding the mixture racemic of crystals in the form of conglomerate, and of bringing the new assemblage to a plateau of temperature $T_B$ during the time necessary to obtain equilibrium thermodynamic so that the point figurative E' is symmetric to E relative to the plane of the mixtures racemic of the system solvent, antipode (−), antipode (+), said point E' being situated in the domain two-phase of the second enantiomer in excess and in equilibrium with its solution saturated;

f) of applying the same law of programming of cooling as in stage (b), to the mixture two-phase prepared in the stage preceding containing the second enantiomer, so that the liquors-mother retain a weak supersaturation during crystallization in order to favor growth of the enantiomer present in the form of crystals, while nucleation spontaneous of the first enantiomer present in the solution;

g) of adapting during the entire duration of growth crystalline of the stage preceding a rate of agitation slightly increasing as a function of time so that it is at any moment sufficiently slow to favor growth of the second enantiomer while avoiding generation of forces of striction too substantial, producing nucleation uncontrolled and sufficiently rapid to obtain a suspension homogeneous and replenishment rapid of the liquor-mother around each crystallite;

h) of collecting the crystals of the second enantiomer;

i) of adding to the liquors-mother resulting from collection crystalline accomplished in the stage preceding it the mixture racemic of crystals in the form of conglomerate to obtain an aggregate whose composition is identical to that of aggregate E initial;

j) of repeating stages (a), (b), (c), (d). (e), (f), (g), (h) and (i) to obtain successively one then the other of the two enantiomers.

Optimization and reproducibility of the process of the invention are achieved owing to the determination of the parameters thermodynamic and kinetic.

Thus, in stage (a) of the process of the invention the choice of the solvents and the range of temperature of operation are defined so as to have simultaneously:

antipodes that produce a conglomerate and whose possible racemate is metastable in the range of temperature of operation;

liquors sufficiently concentrated but of low viscosity and limited pressure of vapor;

absence of solvolysis and racemization;

stability of the solvates if they are present in equilibrium and if they involve enantiomers resolvable.

In stages (a) and (e) of the process of the invention, the temperature $T_B$ is greater than the temperature $T_L$ of homogenization of the amount of mixture racemic contained in the suspension initial and in that from the curve of variation of $T_{HOMO}$ as a function of excess enantiomeric and for a concentration constant of mixtures racemic $X_L$, said temperature $T_B$ is defined so that the weight of the fine crystals of the first enantiomer of stages (a) and (i) and of the second enantiomer of stage (e), in equilibrium with their solution saturated, represents at a maximum 50% and preferably between about 25 and 40% of the recovery expected.

In stages (b) and (t) of the process of the invention the lower programming of cooling of the temperature $T_B$ to $T_F$, adapted to the set-up experimental, is defined in order:

to obtain a weak supersaturation during the entire duration of crystallization of the enantiomer present in the form of crystals at the beginning of each cycle, this weak supersaturation provoking growth and nucleation secondary mild;

to reach at $T_F$ the maximum of supersaturation of the other enantiomer without nucleation primary, to obtain a collection of crystals in stages (d) and (h) which, after addition of the mixture racemic and compensation in stages (e) and (i). permits cyclicity of the operations.

In effect, each set-up experimental influences the capacities of supersaturation of mixtures used and the efficiency of agitation and, as a result, the law of programming of cooling is adapted to circumstances in which the process is used. As regards temperature $T_B$, the solubilities of the mixture racemic as a function of temperature, the curve $T_{HOMO}$ as a function of excess enantiomeric for a concentration constant of mixture racemic $X_L$, are totally independent of the set-up experimental.

The law of programming of cooling, which is the function relating the temperature to time, is determined for its part from $T_L$ to $T_F$ by cooling of the solution of concentration $X_I$ of $T_L+1°$ C. to $T_F$, $T_F$ being less than $T_L-(T_{HOMO}-T_L)$, in order to obtain a solution saturated stable without nucleation primary while permitting recovery double of the excess enantiomeric initial, and in that said law of programming of cooling is determined for its part from $T_B$ to $T_L$ by extrapolation of this same law determined from $T_L+1°$ C. to $T_F$.

The process of the invention presents other characteristics advantageous, alone or in combination, such as:

in stages (a) and (i), the weight of the fine crystals of the first enantiomer in equilibrium with its solution saturated represents between about 25 and 40% of the recovery expected, 50% representing a limit maximum;

in stage (e) the weight of the fine crystals of the second enantiomer in equilibrium with its solution saturated represents between about 25 and 40% of the recovery expected. 50% representing a limit maximum;

in stages (b) and (t) the thermicity accompanying deposition of the first enantiomer and of the second enantiomer is integrated in the law of programming in temperature;

in stages (e) and (i) one carries out compensations in solvent;

in stages (a), (e) and (i) the fine crystals of the mixture racemic in the form of conglomerate which are added are subjected before being introduced to treatment preliminary accelerating the stage of dissolution, such as grinding and screening, treatment with waves ultrasonic, lyophilization partial; these treatments having also the purpose of producing fine crystals capable of generating a surface of growth crystalline elevated;

in stages (a), (e) and (i), comprising dissolution, the rate of agitation is increased with relation to stages (c) and (g).

In addition to the data of equilibria heterogeneous required to employ the process of the invention, the operations remain also subject to constraints kinetic adjustable, especially the law of cooling, which are for each aggregate solvent, enantiomers, a case special.

The process of the invention presents several advantages relative to methods of the art prior:

absence of introduction of nuclei, production of a better recovery of crystals, production of a better purity of crystals, production of a better reproducibility of the operations, possibility of undertaking resolution without having recourse beforehand to separation and purification of the two enantiomers.

a gain of time in each cycle of operation.

The advantages cited above permit also contemplation of a greater ease of automation of the process of the invention relative to methods of the art prior.

A description of the system ternary A (solvent), R and S (antiopodes optical), in equilibrium is necessary before comparing the process classic SIPC, on the one hand, with its variants and, on the other hand, with the process of the invention, designated below AS3PC for "Auto-seeded polythermic preferential crystallization".

This description comprises also examples nonlimiting intended to illustrate other characteristics and advantages of the process of the invention.

As example of use of the process of the invention, will be developed in the specification that follows the resolution of two enantiomers optical: 3,5-dinitrobenzoate-1--phenylethanol, tartrate double of sodium and ammonium tetrahydrate, hydrochloride of acid glutamic, threonine, 5-methyl-5-phenylhydantoin, 5-methyl-5-(4-methylphenyl) hydantoin, 5-ethyl-5-phenylhydantoin, 5-methyl-5-(4-chlorophenyl)hydantoin, threitol, according to an arrangement experimental particular.

It will make reference in the following to drawings enclosed in which:

All the sections isothermal and isopleths represented in these figures possess variable compositions expressed in fractions weight.

DETAILED DESCRIPTION OF INVENTION

I. The Equilibria Heterogeneous Ternary: Antipodes R and S, and Solvent A

For example, the work of J. E. Ricci (Ed. Dover Publication, Inc., New York (1966), "The phase rule and heterogeneous equilibrium") treats the case general of equilibria heterogeneous in systems ternary. The description below will be limited to aspects particular of the system ternary: A (solvent achiral), R and S (enantiomers nonracemizable in the range of temperature exploited), necessary for comprehension of different procedures of crystallization preferential.

In order to reveal the role particular of the solvent this system ternary will be represented by a prism right with section triangle rectangle isosceles, on which the temperature is plotted on an axis perpendicular to the plane of concentrations.

The identity of the variables thermodynamic of the two enantiomers: Tf, ΔHf, solubility in a solvent achiral, etc., means that the representation of domains is symmetric with relation to the plane vertical A-RS-T, uniting the mixtures optically inactive of FIG. 1. In order to facilitate a first description of this system the simplifications following have been adopted:

- the only phases that crystallize are the constituents pure in an arrangement given (absence of racemate, solvate and polymorphism for the antipodes);
- the miscibility between the constituents independent is zero in the state solid;
- the solvent possesses a point of melting distinctly lower than that of the antipodes;
- in the range of temperature employed the solubility of one antipode is not influenced by the presence of the second in the solution (law of Meyerhoffer respected), which is conveyed by a value of the ratio $\alpha=2$).

1. Representation of equilibria ternary as a function of temperature

Figure 1:
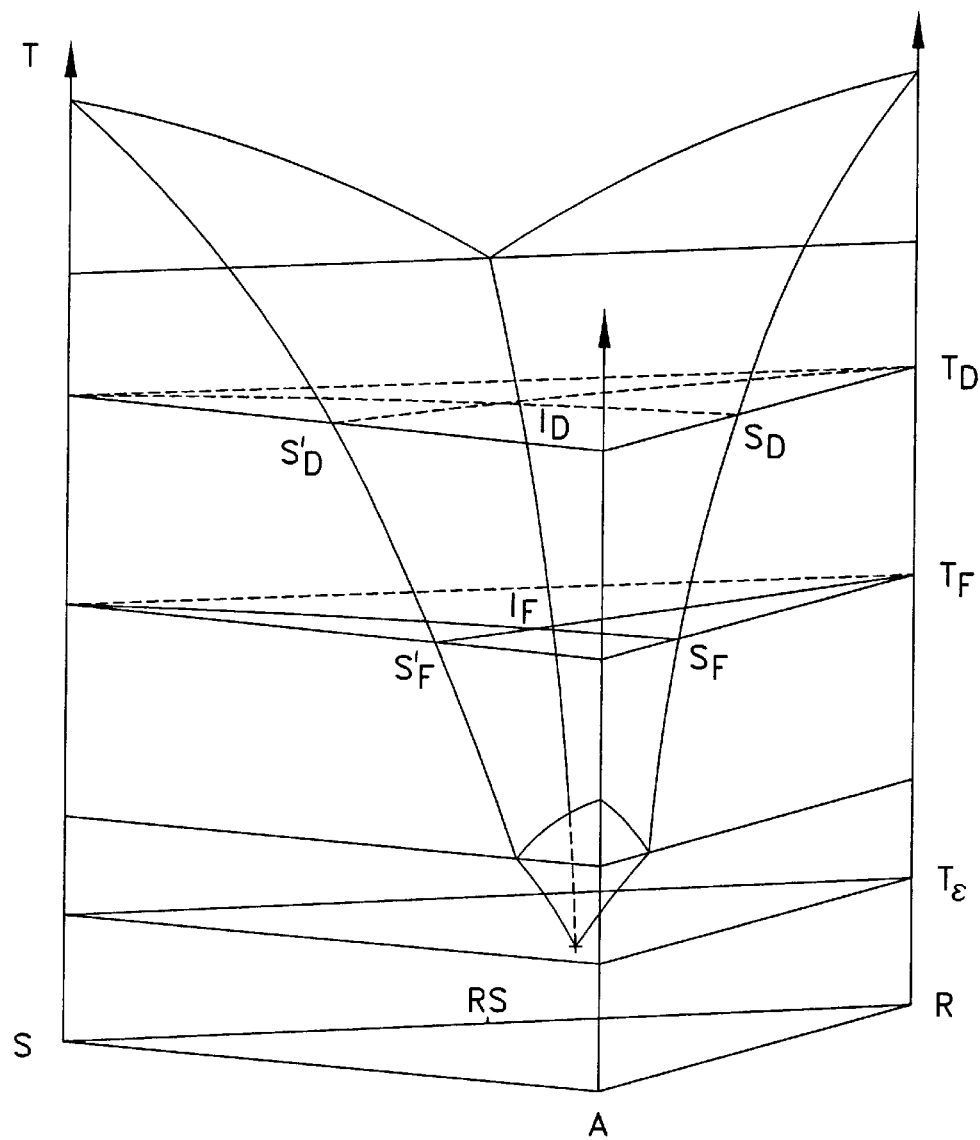
FIG. 1 is a representation in perspective of the system ternary solvent A—antipode R—antipode S, as a function of temperature, as well as surfaces of crystallization of each constituent and compositions of solutions doubly saturated (curves monovariant); on this figure are also shown the isotherms at temperatures $T_D$ and at $T_F$ and the plane of eutexia ternary and the temperature $T_\epsilon$ and enclosing four phases.

FIG. 1 permits visualization of the domains of the phases following:

- the domain monophase of the solution dilute ($\phi=1$);
- three surfaces of crystallization of constituents delimiting the domains two-phase ($\phi=2$). The surface of the deposition of the solvent is confined in the vicinity of A, because the point of melting of this constituent is distinctly lower than that of the other constituents, according to the conditions mentioned previously;
- the three curves monovariant ($\phi=3$) or valleys eutectic issuing from the point eutectic binary;
- the invariant eutectic ternary at Tε ($\phi=4$), below which the three constituents are crystallized.

Figure 2:
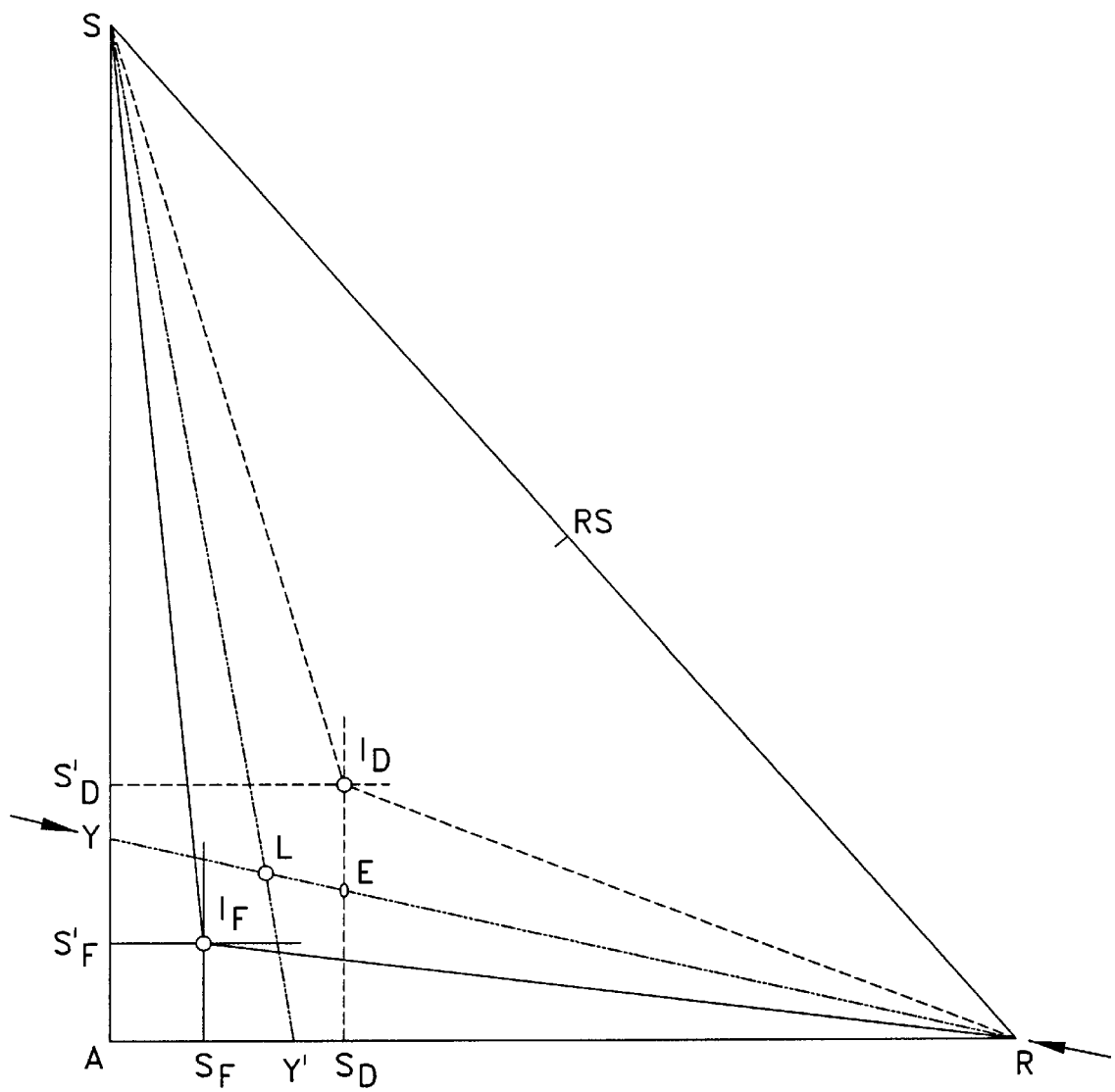
FIG. 2 is a projection on the plane of concentrations of equilibria at $T_D$ and $T_F$; as well as a representation of the trace of the section isopleth RY, on which the point E depicts the composition of the mixture initial slightly enriched in antipode R and before depositing this same antipode.

FIG. 2 represents in fashion superimposed two sections isothermal at $T_D$ and $T_F$ of the ternary visualized in FIG. 1. At each temperature the section is composed of four domains as detailed in the table below.

| Temperature | Limit of domain | Nature of phases in equilibrium | Number of phase in equilibrium |
|---|---|---|---|
| $T_D$ | A-SD-ID-S'D | Solution dilute | 1 |
| $T_D$ | R-SD-ID | Solution + crystals of R | 2 |
| $T_D$ | S-S'D-ID | Solution + crystals of S | 2 |
| $T_D$ | ID-R-S | Solution + crystals of R and S | 3 |
| $T_F$ | A-SF-IF-S'F | Solution dilute | 1 |
| $T_F$ | R-SF-IF | Solution + crystals of R | 2 |
| $T_F$ | S-S'F-IF | Solution + crystals of S | 2 |
| $T_F$ | IF-R-S | Solution + crystals of R and S | 3 |

2. Section isopleth RYT

Figure 3:
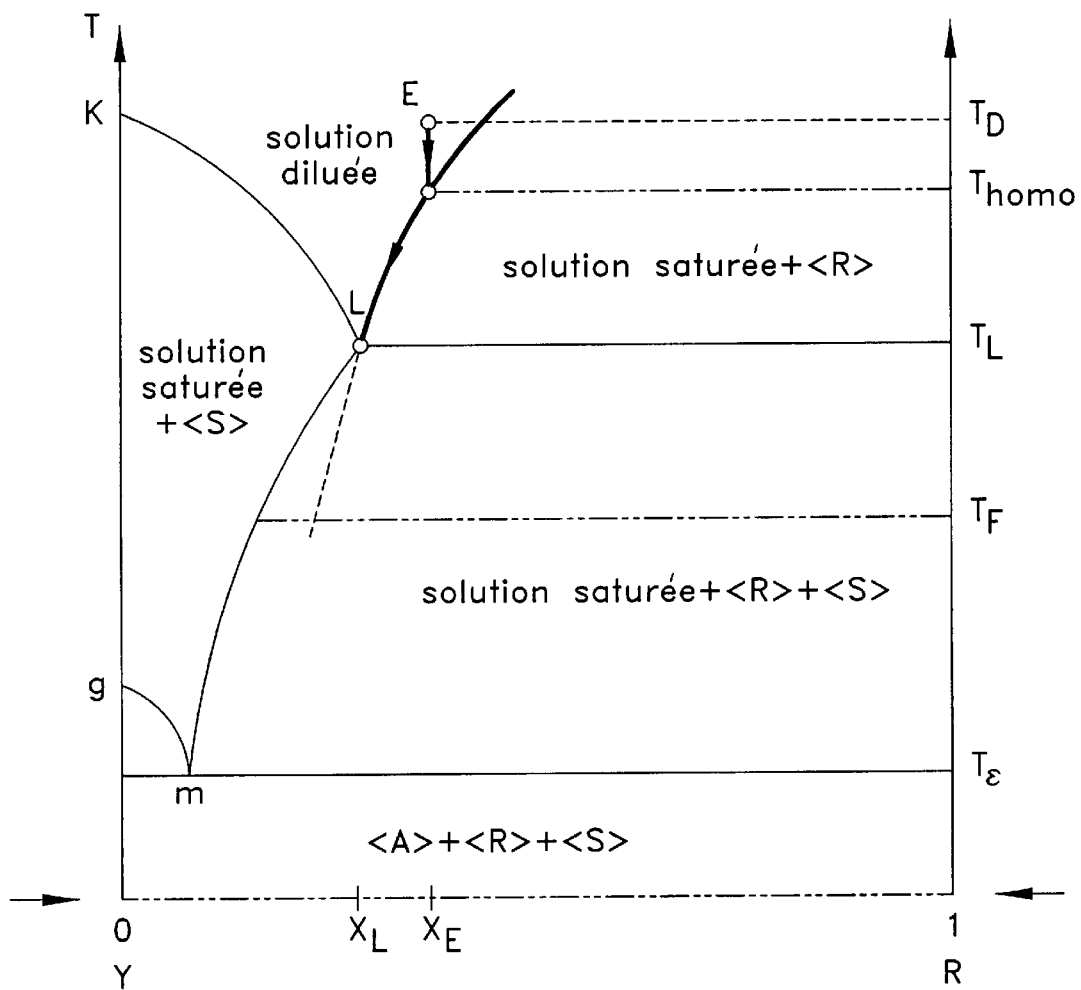
FIG. 3 is the section vertical isopleth RY of FIG. 2 containing the points composition of the antipode in excess and that of the solution initial E, on which is represented the path at equilibrium and during cooling of the point-solution for a mixture of composition $X_E$ (in line solid). For $T<T_L$ the point-solution no longer belongs to this section.

FIG. 3 shows the section isopleth R-Y-T which is fundamental in comprehension of the crystallization conducted by cooling of solutions ternary in quasiequilibrium thermodynamic. The same section is also necessary to follow the processes outside of equilibrium, SIPC, variants and AS3P3. This plane is the locus geometric of points verifying the relation:

$X_A/X_S=(1-Y)/Y$=constant, with $X_A$ and $X_S$ given the fractions weight in solvent and antipodes S.

From FIG. 3, one distinguishes:

The domain one-phase of the solution ternary.

The liquidus of the antipode R, this curve represents the intersection of plane R-Y of FIG. 2 with the surface of crystallization of this constituent. This curve of equilibrium stable gives rise to melting of antipode R (not shown) and is found limited toward the low temperatures by point L, belonging to the valley eutectic ternary of mixtures racemic. This last curve and the trace of the conoid to $T_L$ (segment horizontal to $T_L$) delimit the domain two-phase: solution saturated plus crystals of R; it extends into the domain three-phase subjacent, by a curve of solubility with characteristics metastable of the same antipode R (in lines dashed).

The domain three-phase: crystals of R and of S, plus solutions saturated. This domain is limited at the top by the trace horizontal of the conoid of R toward the bottom by the trace of the plane invariant eutectic ternary, to the left by the trace Lm of one of the conoids related to antipode S.

The trace KL of the surface of crystallization of antipode S which limits in the upper part the domain two-phase: solution saturated plus crystals of S. This domain is limited in the part lower by the traces of the two conoids of S: gm and Lm. The localization of this second trace Lm of the conoid of S relative to the curve of solubility metastable of R extension of EL will be discussed later relative to the position relative of Fl and F as a function of ratio of solubilities α.

The invariant ternary at temperature Tε below which are found the three constituents crystallized A, R and S.

II. Evolution at Cooling and in Quasiequilibrium Thermodynamic of Solutions Ternary Presenting a Weak Excess Enantiomeric It is considered in that which follows that the point aggregate of the system (i.e., the point representing the composition overall of the mixture) is situated on the vertical passing through point E of FIGS. 2 and 3, its position precise is defined by its temperature (or side) T. Only the interval of temperature following is considered:

$T_D$: temperature for which the mixture of original is a solution homogeneous, and $T_F$: temperature of end of crystallization and filtration, situated in the domain three-phase.

This composition overall E corresponds to a solution racemic slightly enriched with a mass M of antipode R and achieving a mass total Mt (excess enantiomeric R−S/R+S is generally between 4 and 9%). The conditions of equilibrium are obtained by cooling very slow and by seeding in phase(s) solid from the point aggregate E figurative of the mixture passes through a range where this (these) phase(s) is (are) present in equilibrium.

At the temperature of initial $T_D$, the solution is homogeneous. On cooling one observes successively:

Crystallization of the antipode R alone, from $T_{HOMO}$ to $T_L$, simultaneously the point solution is displaced on the curve of solubility of antipode R namely from point E to the side $T_{HOMO}$, to point L on the inside of the section isopleth R-Y. At point L the mass M of crystals R in equilibrium with the solution saturated is given by Mt $(X_E-X_L/1-X_L)=M$ and correspond to the excess enantiomeric present in the solution initial (FIG. 3); the abscissas of the points L, E and R correspond to compositions $X_L$, $X_E$ and 1 (FIG. 3).

From $T_L$, the point solution evolves from L to $I_F$ on the curve monovariant containing the solutions of composition racemic, shown in FIG. 2, leaving therefore the section isopleth R-Y of FIG. 3; the crystals of R and of S are deposited then simultaneously and in equal amount.

Resolution cannot be accomplished under conditions of equilibrium for temperatures lower than $T_L$.

Figure 4:
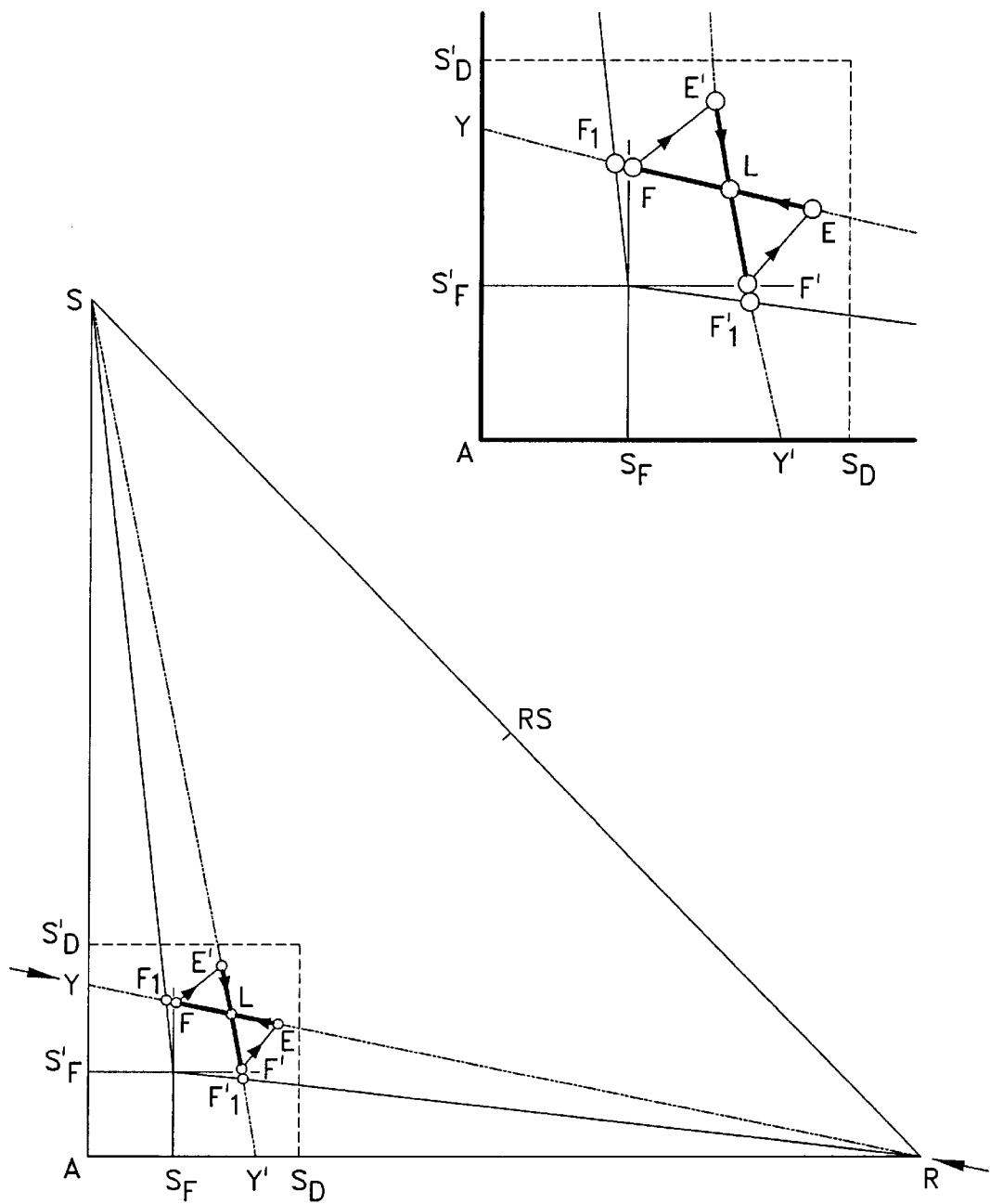
FIG. 4 is a projection on the plane of concentrations of the path of the point-solution (in line solid) during resolution alternated by entrainment isothermal at temperature $T_F$ and seeded according to the method SIPC.
Figure 5:
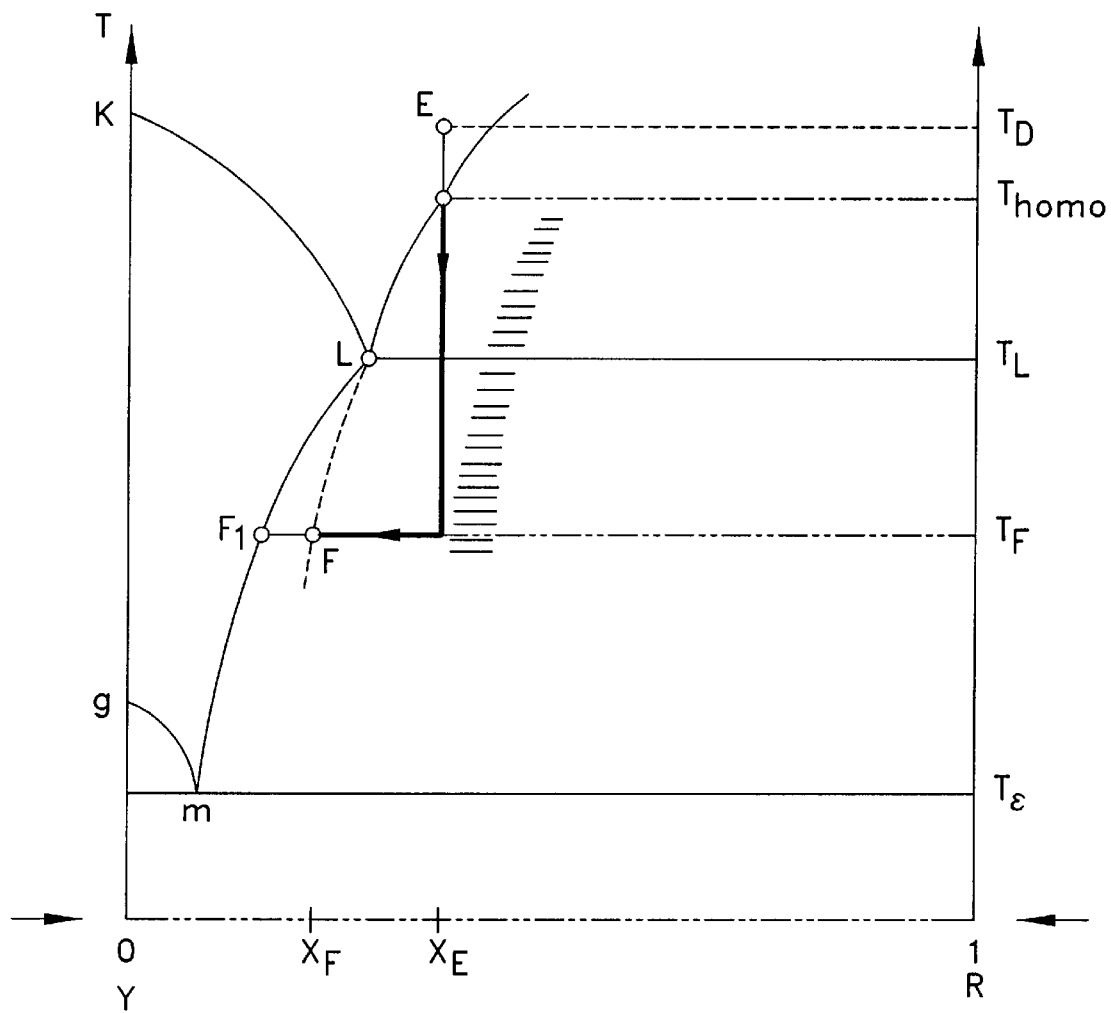
FIG. 5 is the section vertical isopleth containing the line RY of FIG. 4 and illustrating the path of the point-solution (in line solid) of E to F during entrainment isothermal (at $T_F$) and seeded according to the method SIPC.

III. Evolution of Point Solution During Resolution by Entrainment Conventional, According to the Process SIPC 1. Crystallization of first antipode in excess The solution E preceding is homogenized at temprature $T_D$ (FIGS. 4 and 5). In order to make it supersaturated, it is cooled rapidly to the temperature $T_F$ without any crystallization appearing. This solution, outside of equilibrium thermodynamic, is then seeded with nuclei of antipode R very pure of the same chirality as that of the antipode in excess. Crystallization isothermal of antipode R is established and the point representative of the solution evolves to the inside of the section R-Y-T from E to the side $T_F$ with which it is first merged, until F where one proceeds rapidly to filtration. The weight of antipode R recovered is 2M or even equal to $Mt(X_E-X_F/1-X_F)$.

2. Crystallization of second antipode, cyclicity of operations

The operation fundamental preceding has therefore created a solution F enriched in antipode S. By adding a mass 2M of mixture racemic (equal to that of the antipode recovered) and by heating this mixture to the temperature $T_D$, one obtains a solution homogeneous E' symmetric to E relative to the plane vertical A-(RS)-T. The process permitting production of a mass 2M of antipode S will be also represented by a path symmetric to the preceding relative to this plane median. One proceeds therefore in sequence to the operations following:

the solution E' homogeneous at temperature TD is first cooled to $T_F$, then, seeded with nuclei very pure of antipode S; growth of this antipode displaces the point representative of the solution on the segment horizontal E'F' (to side $T_F$);

when the point solution merge with F' the solution is filtered and furnishes a mass 2M of antipode S;

after a new addition of mass 2M of mixture racemic and new heating to $T_D$, one obtains again a solution homogeneous whose point representative has merged with the point initial E on side $T_D$;

the sequence of the process becomes simply a reproducing this cycle of operations.

3. Variants of the process SIPC

The literature (Amiard, G. (1956), Bull. Soc. Chim. Fr. 447; Collet, A., Brienne, M. J., Jacques, J. (1980), Chemical reviews 80, 3, 215–30; Nogushi Institute (1968) Patent Great Britain 1 197 809) rests on the scheme general preceding; the principal modifications apparent in the literature are classified in the manner following:

a) Nucleation primary spontaneous of the antipode in excess

During resolution of the (±) threonine (Amiard, G. (1956), Bull. Soc. Chim. Fr., 447), the nucleation primary of the antipode in excess intervenes spontaneously within the solution homogeneous supersaturated. This nucleation primary occurs when the point E representing the composition of the aggregate is situated in the domain three-phase and the solution is not agitated (Collet, A., Brienne, M. J., Jacques, J. (1980), Chemical reviews, 80, 3, 215–30). The results irregular to which leads this method will be analyzed in comparison with those of the process AS3PC.

b) Seeding during cooling

This protocol is the most frequently encountered in the literature (Noguchi Institute (1968), Patent Great Britain 1 197 809) when the process differs from SIPC. Among the procedures cited differences appear; however, one can delimit the major lines common following:

cooling of the solution homogeneous from $T_D$ to a temperature less than $T_L$ but greater than $T_F$;

seeding with nuclei of the same chirality as the antipode in excess of the solution homogeneous supersaturated situated in the domain three-phase;

cooling to $T_F$. In certain cases this last stage is controlled by programming precise of the temperature (Noguchi Institute (1968), Patent Great Britain 1 197 809).

One will combine these protocols under the same term S3PC for "Seeded polythermic programmed preferential crystallization", although programming of the temperature is nonexistent or limited to the second phase of cooling. The results obtained during resolution of (±) hydrochloride of acid glutamic by the method S3PC (Noguchi Institute (1968), Patent Great Britain 1 197 809) and AS3PC will be compared.

Figure 6:
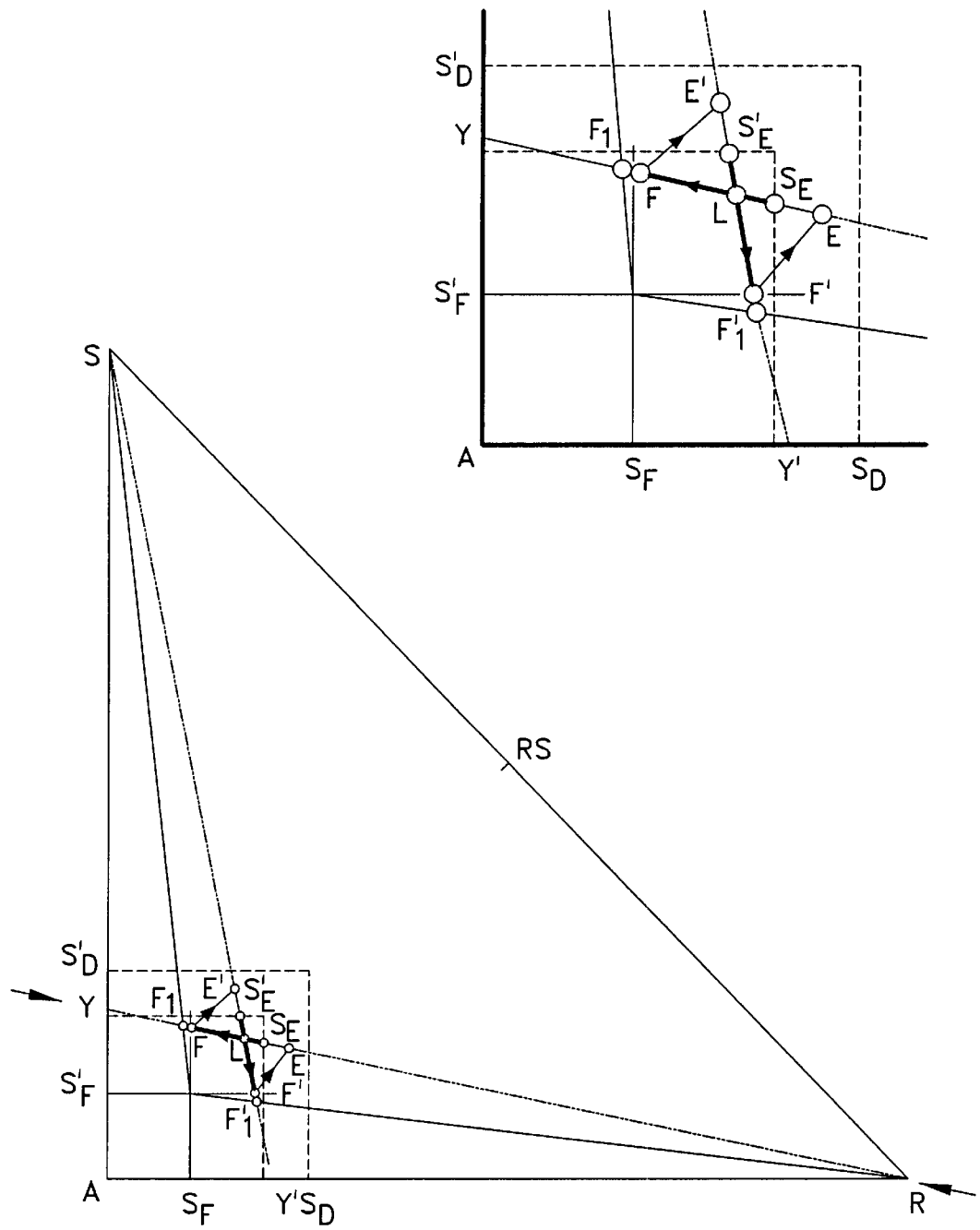
FIGS. 6 and 8 are a projection on the plane of concentrations of the path of point-solution (in line solid) during resolution by the process of the invention polythermal programmed and autoseeded (AS3PC).

IV. Evolution of Point Solution During Resolution by Entrainment Programmed and Autoseeding According to the Process of the Invention AS3PC In order to better compare the processes classic and the process of the invention AS3PC the point initial E is chosen arbitrarily on FIGS. 6 and 7, identical to the case preceding; however, as this will appear in the examples that follow the process of the invention permit taking a point E farther from the plane A-(RS)-T and therefore with an excess enantiomeric more substantial and thus improving the recovery of crystals of each operation.

1. Crystallization of the first antipode in excess

Figure 7:
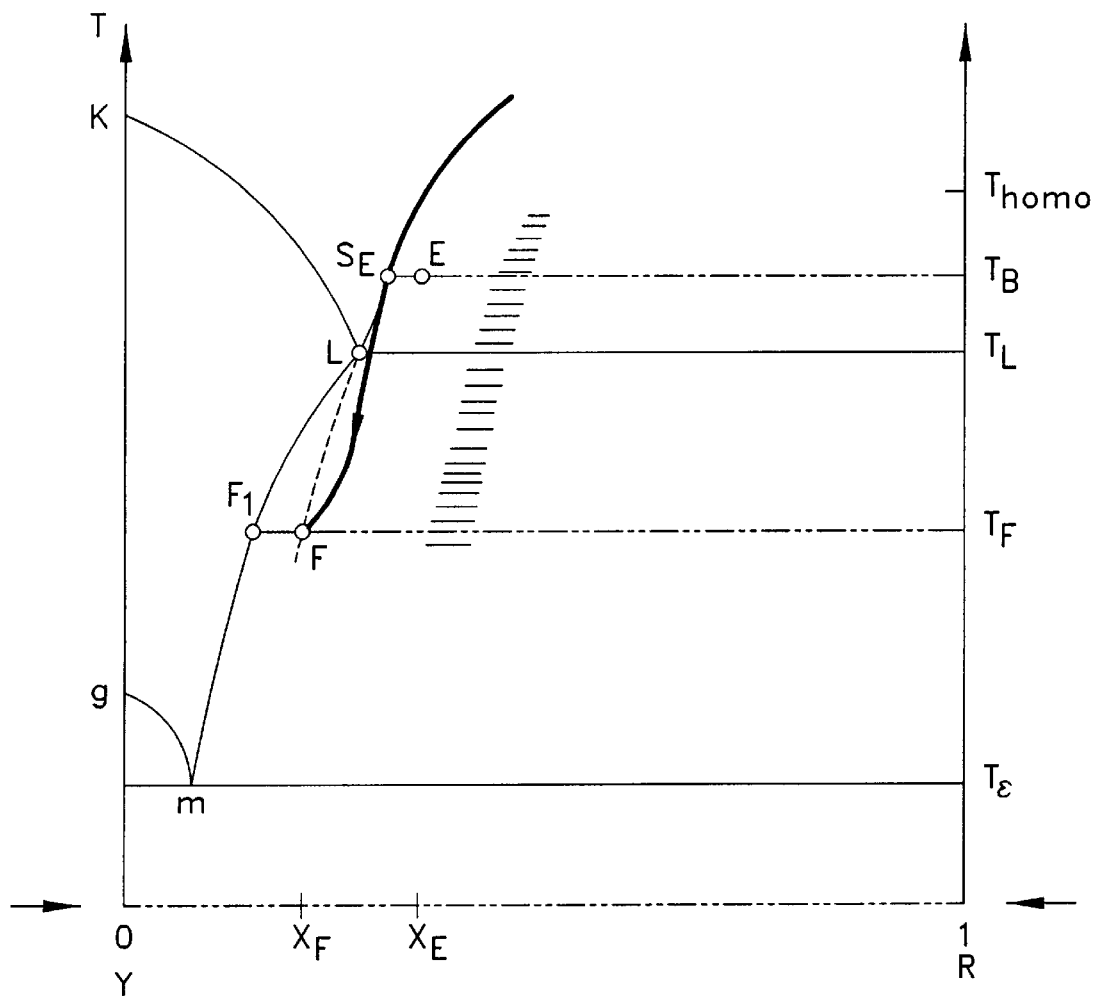
FIG. 7 is the section vertical isopleth containing the line RY of FIG. 6 and illustrating the path of point-solution (in line solid) from $S_E$ to F during resolution by the process of the invention polythermal programmed and autoseeded (AS3PC) and verifying the relation $s(\pm)<2-\alpha$.

At the beginning of the process and contrary to protocols classic, the aggregate, crystals plus solution, is no longer homogenized but is brought to the temperature $T_B$. The solution initial is then in equilibrium with the crystals of enantiomer as an excess (for example R on FIG. 7). The points figurative of the solution (SE and the aggregate (E) are therefore not merged from the beginning of the process. This mixture two-phase is subjected to a law programmed of descent in temperature without addition of nuclei crystalline. The point representative of the solution describes a curve $S_E F$, contained in the plane R-Y-T, dependent on the kinetics of cooling (FIG. 7). With a kinetics correctly adjusted one obtains at the beginning a growth of the crystals of enantiomer in excess, crystallization evolves then toward a regime simultaneous of growth plus nucleation secondary. When the point representative of the solution reaches point F, one proceeds to filtration to recover a mass 2M of crystals of antipode R.

2. Crystallization of the second antipode, cyclicity of the operations

From point F, which corresponds to the solution-mother preceding, one passes to point E', symmetric to point E relative to the plane vertical A-(RS)-T, by addition of a mass 2M of mixture racemic and heating to a temperature $T_B$. The excess enantiomeric is exploited to be placed in the domain two-phase containing the solution saturated and the crystals of the antipode in excess. Beforehand, the mixture racemic added during passage from F to E' (like from F' to E) will be ground and screened in order to accelerate the stage of dissolution of the two antipodes and more particularly of the antipode in deficit, and permit thus the formation of a number substantial of crystals of the antipode in excess, playing the role of seeds introduced during the processes classic.

The solution saturated $S'_E$, symmetric to $S_E$ relative to the plane A-(RS)-T. is subject to the same law of cooling. The crystals present from the beginning of cooling grow and participate then in a double mechanism of growth plus nucleation secondary. As in the case of the first crystallization, no seeding is therefore necessary.

During this time, the point representative of the solution is displaced on a curve $S_{E'} F'$ contained in the plane of the section isopleth S-Y'-T symmetric relative to the plane bisector A-(RS)-T.

At the moment where the solution acquires the point representative situated in F', on proceeds to filtration to recover a mass 2M of crystals of antipode S. A new addition of a mass 2M of mixture racemic ground and screen followed by elevation of the temperature to $T_B$ returns the mixture two-phase to equilibrium initial.

Continuation of the process comes down then to repeating this cycle of operations, producing alternately the crystals of antipodes R and S.

3. Conditions necessary for use of the process AS3PC a) The mixture equimolar of antipodes optical produces in the solvent used and for the interval of temperature $T_B$–$T_F$ a conglomerate (antipodes pure or solvates); however, the existence of a racemate metastable is not a handicap (case of tartrate of sodium ammonium tetrahydrated).

b) The molecules to be resolved are stable in this solvent and in the range of temperature used between $T_B$ and $T_F$.

c) The examples below demonstrate that a determination of the temperatures of equilibrium ternary $T_L$ and $T_{HOMO}$ is necessary. The temperature $T_L$ is the temperature of dissolution of the mixture racemic in the absence of any excess enantiomeric in the solution. $T_L$ being determined, the temperature $T_{HOMO}$ corresponds to the temperature of homogenization of the solution. It depends on the excess enantiomeric initial and on the ratio α of solubilities of the mixture racemic and the antipode at $T_L$. Knowledge of the capacities of supersaturation of solutions between $T_L$ and $T_F$ is also necessary, according to the kinetics of cooling, the method of agitation, the nature of the vessel and the particle size of the crystals of the antipode in excess. As a first approximation, the time of appearance of crystals by nucleation primary in the solution racemic L homogeneous, cooled from a temperature slightly greater than $T_L$ with the same kinetics, gives an indication concerning the capacity of supersaturation tolerated by the conglomerate under these conditions experimental. This method of operation has been considered in the examples.

d) The knowledge of the kinetics of dissolution of a mass known of mixture racemic (of particle size given) dispersed in the solution at temperature $T_B$. Some tests are sufficient to understand this duration.

4. Importance of process of the invention AS3PC relative to the processes SIPC, S3PC or their variants The examples below demonstrate that the process AS3PC is well adapted to different classes of enantiomers susceptible of being resolved: compound covalent or with character ionic, solvated or not.

The results obtained illustrate the advantages of this process relative to processes SIPC, S3PC and all the variants, in particular:

removal of the constraint of seeding, improvement of yield and of the purity optical, better reproducibility of each crystallization, reduction of the duration of each cycle.

A discussion systematic of these advantages is detailed below.

a) Removal of the constraint of seeding

The nuclei necessary for each crystallization are here constituted of crystals in equilibrium in the domain two-phase: solution saturated+crystals of the antipode in excess. This phase crystalline possesses therefore a priori a purity optical maximum. In the case of solution solid limited, achievement of equilibrium permits having the purity optical maximum of the seeds of the nuclei in the solution at this temperature.

The process AS3PC not requiring introduction of nuclei, less dust or impurities solid are introduced to the media (there will in fact only be those introduced with the mixture racemic ground and screened).

The crystals formed in situ are at the outset well dispersed in the solution subjected to agitation.

During use of the process AS3PC, only a mixture partially enriched is necessary; for example, the form chiral natural (case of tartrate) or that obtained by diastereoisomerism with an agent of resolution natural, such as an alkaloid natural. From the second manipulation and for all the following, the absence of introduction of nuclei renders null the necessity to isolate and purify the second antipode.

The principle of autoseeding according to the process of the invnetion AS3PC can be extended to separation of salts diastereoisomeric, enantiomers one from the other and accomplishing for the interval of temperature defined the pair stable in the system quaternary reciprocal of two pairs of salts diastereoisomeric in the presence of the solvent.

b) Improvement of purity and yield

The temperature $T_B$, chosen as a first approximation as being equal to the average of the values $T_{HOMO}$ and $T_L$, one can (by assuming a variation linear of solubility in this narrow interval of temperature) consider that the weight of the nuclei in the state initial represents a quarter of the weight of the crystals obtained on each recovery. In most cases one can, by adjusting $T_B$ closer to $T_L$, have up to 40% of the weight of the recovery final present in the form of fine crystals. This is easy to accomplish when the variation of $T_{HOMO}$ as a function of excess enantiomeric presents a slope sufficient and the excess enantiomeric originating from each filtration is substantial (as this has been shown in certain of the examples below). At any rate 50% represents the limit that one can reach at equilibrium; in this case the temperature $T_B$ will be equal to the temperature $T_L$. This mass important of fine crystals permits, when the temperature diminishes, to obtain a large surface equivalent of crystals and therefore to favor the process of growth rather than to induce directly a nucleation at high supersaturation as in the process SIPC and to a lesser extent in the processes grouped under the name S3PC.

The law of programming of the decline in temperature permits control of the process of growth, on the one hand, and nucleation+growth, on the other hand, in order to adapt to each case special. A kinetics slow of cooling will permit at the point representative of the point-solution shifting as close as possible of the curve of solubility to the character stable then metastable of the antipode (Mullin, J. W. (1972), Ed. Butterworth). In the case where the nucleation secondary of the antipode in excess is difficult (case of resolution of (±) hydrochloride of acid glutamic) (Noguchi Institute (1968), Patent of the United Kingdom No. 1 197 809), this advantage is decisive.

For a same point overall of departure, the process AS3PC permits therefore at the point figurative of the solution to remain farther from the zone so-called labile of metastability of Ostwald (zone shaded of nucleation spontaneous of enantiomers and/or of racemate metastable possible, of FIGS. 5 and 7) than the process SIPC and its variants. The process AS3PC will be therefore the best adapted in the cases difficult for use where appear constraints additional, like:

the capacities of supersaturation of the solutions quasiracemic are limited, the ratio α is unfavorable, the existence of a racemate metastable but possessing a high rate of nucleation primary in the range of temperature utilized.

This means still that for a pair of enantiomers given, that is to say a same capacity of supersaturation and a same ratio of solubility a, the process AS3PC permits attainment of a better yield. Crystallization of each antipode can be pursued longer without the point solution reaching the composition defined by the limit of Ostwald. The process AS3PC permits therefore affecting mixtures E, F, E', F', of the beginning and end of crystallization, an excess enantiomeric more substantial than in the process SIPC or its variants. A crystallization more slow permits also obtaining solids presenting fewer defects of structure and especially inclusions of solutions-mother, in the crystals. All the examples demonstrate thus an improvement of purity optical of the crystals.

Figure 8:
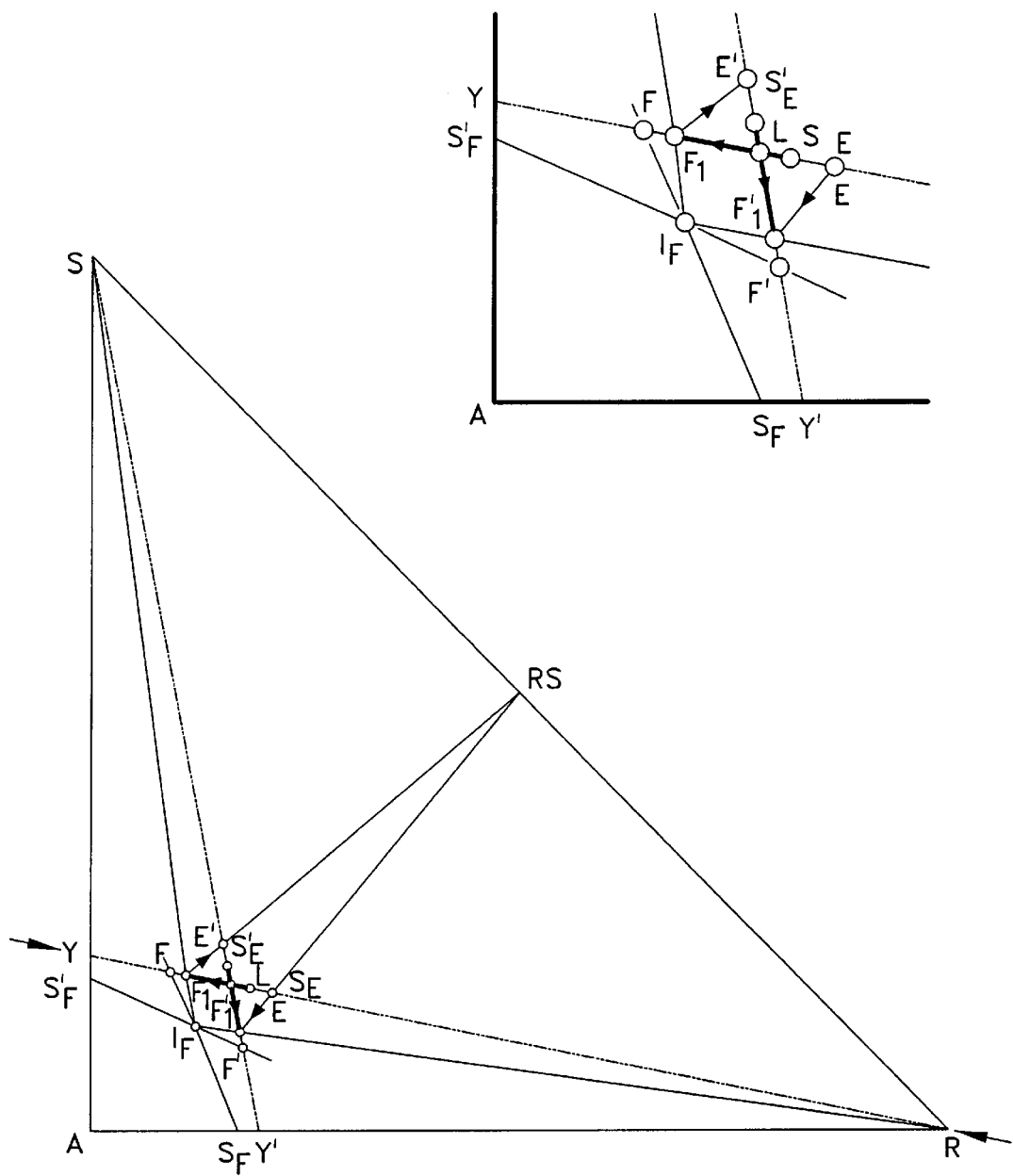

For a ratio α such that $S(\pm)<2-\alpha$ (α=ratio of solubilities of mixture racemic and the antipode at $T_F$: $\alpha=S(\pm)/S_{(R)}$), the point $F_1$ can be substituted at point F for the end of filtration. In a manner general, for a section isopleth given, it is from $F_1$ and F the point of more weak excess enantiomeric that practically will represent the composition final of the liquors-mother subjected to filtration (FIG. 8):

c) Better reproducibility

The parameters: time of holding at the temperature $T_B$, value of the excess enantiomeric, particle sizes of crystals at $T_B$, rate and method of agitation, law of programming of decline in temperature being defined, the process AS3PC exhibits a good reproducibility. The size of the crystals can be adjusted and one can in particular modulate the parameters in order to avoid the existence of crystals of size reduced (fine) hampering filtration.

Use of a temperature maximum lower during a time limited, $T_B<T_D$, implies that the process AS3PC will avoid, better than the process SIPC or its variants, the degradation and racemization of antipodes in the case of a fragility of the molecules being resolved in the solvent used. This property concerns also the solvent and it can prove substantial to the extent where the solutions-mother are recycled permanently.

d) Duration of each cycle

The stage of homogenization of the solution-mother (at $T>T_{HOMO}$) being nonexistent, the process AS3PC contributes directly to a gain in energy and times of each cycle shorter, because the growth is established from a mass substantial of crystals and this from the beginning of cooling. This gain is appreciable if the mixture racemic introduced after each filtration is finally ground and screened (preferably a short time before addition).

The stage of dissolution of the mixture racemic (in fact the antipode in deficit more than the antipode in excess in the solution coming from filtration), can be further accelerated by heating during a time limited to a temperature $T>T_B$, followed by return rapid to $T_B$. The time is adjusted so that all the antipode in excess is dissolved in a time minimum. This time depends on the kinetics of dissolution with, for parameter:

the weight and particle size of the mixture racemic,
the law of programming of the temperature,
the type and rate of agitation, all the other parameters being fixed.

This operation has for effect (as also waiting to establishment of equilibrium at $T_B$, but for the latter in a fashion less pronounced) of dissolving the crystals more fine, which presents the drawback of reducing the surface available for growth. This effect will be strongly limited by grinding and screening of the mixture racemic added to each stage, and a rate of agitation substantial. If necessary, one uses ultrasound (considering its effect thermal) in order to obtain a spectrum granulometric finer, more homogeneous and reproducible. One can also use a mixture racemic obtained by lyophilization partial in order to accelerate the stage of dissolution and to have a spectrum of particle size fine of crystals of initial.

Control of parameters improves the reproducibility of crystallization and facilitates therefore a study of automation of the process.

V. Examples

1. Apparatus experimental

The operations are carried out alternately in two tubes about 12 cm of height and 29 mm of diameter with neck ground (29/32 No. 4). These tubes are equipped in their part upper with a tube lateral to establish a vacuum necessary during filtration. The crystals are recovered on glass sintered No. 2 or 3, adaptable on each tube by means of a ring of rubber. Agitation is ensured by a bar magnetic. The liquors pass successively through from one tube to another. These transfers, reduced to a maximum, do not prevent losses between each operation. The more the amounts of product used are low, the more the losses will be proportionately large. One can classify them into two categories:

Losses at the level of glass sintered and in the tube initial of liquor-mother containing excess enantiomeric of the end of crystallization. Compensation is acomplished by addition of crystals racemic and solvent so that this addition corresponds to mixture L, as indicated in the tables of results at the level of the column compensation.

Losses of solvent essentially due to filtration created by vacuum. Compensation is accomplished by adding to each operation solvent additional.

In certain cases, for example when one uses a solvent very volatile, the process of compensation must be more precise. A small amount of the solution is sampled in order to determine the composition, permitting then a compensation rigorous.

In order to achieve a good reproducibility of results, the liquid heat-transfer circulating in the double jacket of the chamber of crystallization is controlled in temperature with a precision of ±0.1° C. The apparatus employed permits fixing a law of cooling reproducible.

The examples below treated by crystallization discontinuous (or in batch) can be on the same principle in fashion continuous or semicontinuous.

2. Resolution of 3,5-dinitrobenzoate-1-phenylethanol

This ester, derivative crystallized of 1-phenylethanol (Synthon chiral ordinary), was the object of a separation by the method classic (Brienne, M. J., Collet, A. and Jacques, J. (1983), Synthesis 9, 704–5). The resolution of this derivative covalent was repeated by comparing the methods SIPC and AS3PC.

a) Characteristics of the product

Temperature of melting of the antipode: 123° C.

Temperature of melting of the mixture racemic: 95° C.

Capacity rotatory specific at 20° C., c=1 g/100 mL, toluene.

| λ (nm) | 436 | 589 |
|---|---|---|
| $[\alpha]^{20}$ (°) | 93.9 | 39.0 | b) Resolution by the method AS3PC

Conditions related to equilibria

Solubility in toluene of mixtures racemic:

| T (° C.) | 20 | 27.9 |
|---|---|---|
| Solubility (% weight) | 27.4 | 34.6 |

Solublity of the antipode pure (−): 13.2% at 20° C.; ratio α=2.07.

Coordinates of point L: concentration=34.6% weight, temperature=27.9° C.

Evolution of $T_{HOMO}$ with excess enantiomeric: (mixture racemic/(solvent+mixture racemic))=34.6%=constant

| % Antipode (−) | 0 | 3 | 5 | 7 | 9 |
|---|---|---|---|---|---|
| $T_{HOMO}$ (° C.) | 27.9 | 30 | 31.2 | 32.3 | 33.6 |

Conditions related to kinetics

Temperature $T_B$: 29.5° C.

Temperature $T_F$: 19.5° C.

Law of cooling: T=f(t):

| T (°) | 29.5 | 28.1 | 25.1 | 22.1 | 19.5 |
|---|---|---|---|---|---|
| t (mn) | 0 | 10 | 20 | 30 | 40 |

Duration of state of supersaturation of solution L subjected to this law of cooling: about 60 minutes for a rate of agitation of 250 rpm.

Duration of crystallization: 42 minutes.

Conditions initial

Excess enantiomeric initial: 9%.

| Weight solvent (g) | Weight (±) (g) | Weight (−) (g) |
|---|---|---|
| 25.05 | 13.25 | 1.31 |

Duration of plateau at $T_B$: 60 minutes.

Rate of agitation: 125 rpm at 29.5° C.; 225 rpm at 19.5° C.

Results

Owing to a size substantial of the crystals, filtration, carried out on a frit no. 2 is easy.

| No. | Weight antipode pure (g) | % Purity optical | Compensation sol. (±) 34.6% |
|---|---|---|---|
| 1 | 2.46 | (−) 88.8 | 1.86 |
| 2 | 2.40 | (+) 94.3 | 1.01 |
| 3 | 2.36 | (−) 94.4 | 1.86 |
| 4 | 2.55 | (+) 85.9 | 1.96 |
| 5 | 2.48 | (−) 87.0 | 1.26 |
| 6 | 2.38 | (+) 94.3 | 1.46 |
| 7 | 2.61 | (−) 90.6 | 1.50 |
| 8 | 2.68 | (+) 94.2 | 1.09 |
| 9 | 2.36 | (−) 88.6 | 1.66 |
| 10 | 2.28 | (+) 92.0 | — |

After each entrainment, and beyond compensation in solution racemic, indicated in the table below, it was added an average of 0.7 g of toluene.

Weight average of crystals of antipode pure: 2.55 g.

Excess enantiomeric average: 1.23 g i.e., 8.5%, i.e., another 9% without loss of solution-mother.

Purity optical average: 91%.

c) Resolution by the method SIPC
Conditions initial

The first entrainment by the method SPIC is carried out on a solution having an excess enantiomeric of 8.87%.

Temperature $T_D$: 35° C.

Temperature $T_F$: 20° C.

Time at $T_F$ before introduction of nuclei: 5 min.

Weight of nuclei: 20 mg.

Time of crystallization: 15 minutes.

Results

Filtration on a frit no. 2 is less easy than by the process of the invention, because of the fineness of the crystals.

Beyond 10 minutes of crystallization the aggregate solution plus crystals acquires the appearance of a gel, agitation no longer homogeneous over the entire height of the tube, despite an increase in rate of agitation.

| No. | Weight antipode pure (g) | % Purity optical | Compensation sol. (±) 34.6% |
|---|---|---|---|
| 1 | 1.76 | (−) 75.8 | 2.11 |
| 2 | 1.28 | (+) 64.1 | 1.99 |
| 3 | 1.63 | (−) 69.9 | 2.54 |
| 4 | 1.65 | (+) 74.0 | — |

Weight average of antipode pure: 1.58 g.

Excess enantiomeric average: 0.79 g, i.e., 5.63%.

Purity optical average: 70.9%.

d) Results obtained by Brienne, J. M. et al. (Synthesis 9 (1983) 704–5)
Initial conditions

| Weight solvent (g) | Weight (±) (g) | Weight (−) (g) |
|---|---|---|
| 125.4 | 66.2 | 4.4 |

Concentration of mixture racemic: 34.6%.

Excess enantiomeric initial: 6%.

Temperature $T_B$: 60° C.

Temperature $T_F$: 20° C.

Weight of nuclei: 100 mg.

Time of crystallization: 60 min.

Rate of agitation: 150 rpm.

Results

Weight average of antipode pure: 8.3 g, i.e., by returning to the same weight of solution racemic and used for the tests, 1.66 g.

Excess enantiomeric average: 4.15 g, i.e., 5.89%.

Purity optical average: 83%.

The results obtained with the method SIPC are worse than those observed with the same process SIPC by Brienne et al. (Synthesis 9 (1983) 704–5) for the reasons following:

The method was used with weights five times lower, which requires a ratio surface/volume less favorable.

The losses due to filtration remain equivalent in weight whatever the weight total employed. They are therefore proportionately higher in this case.

Agitation used by Brienne, M. J. et al. is a coil, not producing therefore friction on the walls of the vessel of glass. In effect, the friction induces strong nucleation, this is why the time of crystallization in the case of the present example (15 min) for a solution initial identical is distinctly lower than 60 min indicated by the authors.

It is suitable to note that these conditions unfavorable are also present during the use of the method AS3PC. The results distinctly better obtained with the method of the invention demonstrate that it offers relative to the results obtained with the method SIPC under conditions more favorable advantages significant which compensate very largely for these handicaps.

3. Resolution of tartrate double of sodium and of ammonium tetrahydrated a) Characteristics of the product It involves a salt of Pasteur whose equilibria of the ternary system R-S-H$_2$O exhibit the existence of a racemate stable of the formula (±)NaNH$_4$(CHOHCOO)$_2$, 2H$_2$O (salt of Sacchi), from 27° C. This compound intermediate has character metastable in the range of temperature between 12 and 18° C.

Capacity rotatory specific, 20° C., c=1 g/100 mL, water.

| λ (nm) | 365 | 589 |
|---|---|---|
| $[\alpha]^{20}$ (°) | +60.4 | +23.3 | b) Resolution by the method AS3PC
Conditions related to equilibria

Solubilities in water of mixtures racemic:

| T (° C.) | 12 | 16.0 | 16.3 | 17.3 |
|---|---|---|---|---|
| Solubility (% weight) | 42.5 | 45.0 | 46.0 | 46.5 |

Solubility of the antipode R: 32% at 12° C.; ratio α=1.33 at 12° C.

Coordinates of point L: 46% weight, temperature 16.3° C.

Evolution of $T_{HOMO}$ with excess enantiomeric: (mixture racemic/(solvent+mixture racemic))=46%=constant.

| T (° C.) | 17.3 | 17.0 | 16.5 | 15.4 | 14.0 | 13.0 | 12.1 | 12.0 | 12.0 |
|---|---|---|---|---|---|---|---|---|---|
| Time (min) | 0 | 3 | 5 | 8 | 12.5 | 16 | 20 | 25 | 30 |

Conditions related to kinetics
Temperature $T_B$: 17.3° C.
Temperature $T_F$: 12° C.
Law of cooling: T=f(t):

| T (° C.) | 17.3 | 17.0 | 16.5 | 15.4 | 14.0 | 13.0 | 12.1 | 12.0 | 12.0 |
|---|---|---|---|---|---|---|---|---|---|
| Time (min) | 0 | 3 | 5 | 8 | 12.5 | 16 | 20 | 25 | 30 |

The duration of the state of supersaturation of the solution homogeneous L subjected to this kinetics is greater than 40 minutes for a rate of agitation of 150 rpm.
Duration of crystallization: 20 min, except in the case of operations 14 to 16 for which the duration is 21.5 min.
Conditions initial
Excess enantiomeric initial: 4.5%.

| Weight solvent (g) | Weight (±) (g) | Weight (+) (g) |
|---|---|---|
| 567 | 4.83 | 0.23 |

Duration of plateau at temperature $T_B$: 40 min for a mixture racemic ground on a sieve of 250 μm a few minutes before introduction into the tube of cystallization.
Rate of agitation: 150 rpm.
Results

| No. | Weight antipode pure (g) | % Purity optical | Compensation sol. (±) 34.6% |
|---|---|---|---|
| 1 | 0.47 | (+) 94.7 | 0.50 |
| 2 | 0.52 | (−) 94.4 | 0.85 |
| 3 | 0.53 | (+) 96.1 | 0.70 |
| 4 | 0.56 | (−) 92.5 | 0.88 |
| 5 | 0.55 | (+) 95.5 | 0.64 |
| 6 | 0.56 | (−) 91.1 | 0.66(i) |
| 7 | 0.59 | (+) 97.2 | 0.62 |
| 8 | 0.59 | (−) 97.5 | 0.79 |
| 9 | 0.52 | (+) 97.1 | 0.60 |
| 10 | 0.53 | (−) 96.0 | 0.72 |
| 11 | 0.56 | (+) 96.1 | 0.64 |
| 12 | 0.53 | (−) 94.4 | 0.58 |
| 13 | 0.52 | (+) 96.0 | 0.70(i) |
| 14 | 0.61 | (−) 97.0 | 0.64 |
| 15 | 0.62 | (+) 96.7 | 0.56 |
| 16 | 0.61 | (−) 95.4 | — |

The crystals obtained at each end of the process are easily filterable on a frit no. 2; they retain very little solution-mother, as shown by the purities optical, despite the concentration elevated of the liquors.

In addition to losses ordinary, one observes, for this compound losses of ammonia due also to filtration by vacuum. The compensation is carried out by addition of 40 mg approximately of a solution of ammonia concentrated which leads to a slight excess in cation ammonium; this is noted (i) in the column compensation of the table above. This excess of ammonia improves slightly the purity of the crystals recovered. In the case of a deficit of ammonia, a turbidity very fine, persisting even to 20° C., manifests itself in the liquors.

Weight average of crystals of antipode pure (manipulations 2 to 13): 0.55 g.

Excess enantiomeric average: 0.27 g, i.e., 5.3%.

Purity optical average: 95.5%.

Despite the existence of a racemate metastable and the limited amounts of solution racemic employed (10.5 g), the method AS3PC gives therefore good results with this hydrate.

b) Resolution by the method SIPC
Conditions initial

| Weight solvent (g) | Weight (±) (g) | Weight (+) (g) |
|---|---|---|
| 5.67 | 4.83 | 0.23 |

Concentration of solution racemic: 46%.

Excess enantiomeric initial: 4.5%.

Temperature $T_D$: 18.6° C.

Temperature $T_F$: 12° C.

Time at $T_F$ before introduction of nuclei: 10 to 12 minutes.

Weight of nuclei: 5 mg.

Time at crystallization: 10 min.
Results
Filtration on frit no. 2.

| No. | Weight antipode pure (g) | % Purity optical | Compensation sol. (±) 34.6% |
|---|---|---|---|
| 1 | 0.38 | (+) 92 | 0.51 |
| 2 | 0.42 | (−) 88 | 0.55 |
| 3 | 0.39 | (+) 92 | 0.57 |
| 4 | 0.39 | (−) 94 | — |

Weight average of antipode pure: 0.40 g.

Excess enantiomeric average: 0.20 g, i.e. 4%.

Purity optical average: 91.5%.

The method AS3PC furnishes better results especially for the weights in crystals of antipode pure.

4. Resolution of hydrochloride of acid glutamic

The Patent English No. 1 197 809 in the name of Noguchi Institute describes resolution of this salt of acid glutamic by using a process polythermal with seeding of the solution homogeneous (S3PC).

a) Characteristics of the products

| λ (nm) | 365 | 589 |
|---|---|---|
| $[\alpha]_{20}$ (°) H$_2$O | 74.7 | 20.6 |
| $[\alpha]_{20}$ (°) HCl, 1N | 94.5 | 26.3 | b) Resolution by the method AS3PC
Conditions related to equilibria
Solubility of the mixture racemic in water:

| Temperature (° C.) | 30 | 42.8 |
|---|---|---|
| Solubility (% weight) | 37.5 | 49 |

Coordinates of point L: 49% weight; temperature: 42.8° C.

Evolution of $T_{HOMO}$ with excess enantiomeric: (mixture racemic/(solvent mixture racemic))=49%=constant.

| % Antipode | 0 | 3 | 4.5 | 6 | 9 |
|---|---|---|---|---|---|
| $T_{HOMO}$ (° C.) | 42.8 | 45.0 | 46.8 | 48.1 | 51.1 |

Conditions related to kinetics
Temperature $T_B$: 44.4° C.
Temperature $T_F$: 30° C.
Kinetics of cooling: T=f(t):

| t (min) | 0 | 15 | 45 | 55 |
|---|---|---|---|---|
| T (° C.) | 44.4 | 37.0 | 32.0 | 30.0 |

The duration of the state of supersaturation of the solution L subjected to this kinetics: 120 min for a rate of agitation of 150 rpm.
Duration of crystallization: 55 min.
Conditions initial
Excess enantiomeric initial: 9.24%.

| Weight solvent (g) | Weight (±) (g) | Weight (+) (g) |
|---|---|---|
| 20.50 | 19.50 | 1.99 |

Duration of plateau at $T_B$: 30 min.
Rate of agitation: 150 rpm at the beginning of crystallization, then 250 rpm at the end.
Results
Filtration on frit no. 3.

| No. | Weight antipode pure (g) | % Purity optical | Compensation sol. (±) 34.6% |
|---|---|---|---|
| 1 | 3.88 | (+) 93.6 | 2.26 |
| 2 | 3.97 | (−) 95.6 | 2.86 |
| 3 | 4.40 | (+) 94.8 | 2.01 |
| 4 | 4.27 | (−) 94.9 | 1.36 |
| 5 | 4.43 | (+) 94.9 | 1.77 |
| 6 | 4.52 | (−) 94.5 | 1.34 |

-continued

| No. | Weight antipode pure (g) | % Purity optical | Compensation sol. (±) 34.6% |
|---|---|---|---|
| 7 | 4.73 | (+) 96.0 | 1.60 |
| 8 | 4.53 | (−) 91.8 | 1.30 |
| 9 | 4.43 | (+) 97.1 | 1.35 |
| 10 | 4.72 | (−) 96.2 | — |

Weight average of antipode pure: 4.50 g from manipulation no. 3.
Excess enantiomeric average: 2.25 g, i.e., 10.34%.
Purity optical average: 95%.

c) Results obtained by the method S3PC descrived in Patent English No. 1 197 809 by the method S3PC
Conditions initial

| Weight solvent (g) | Weight (±) (g) | Weight (+) (g) |
|---|---|---|
| 26.10 | 25.18 | 2.75 |

Concentration of mixture racemic: 51.7% weight.
Excess enantiomeric initial: 9.8%.
Temperature $T_D$: 56° C. (solution homogeneous).
Temperature $T_F$: 32° C.
Weight of nuclei introduced: 1 g.
Rate of cooling: 5 to 8° C./hour.
Duration of crystallization: 150 min.
Results
Weight of antipode pure: 5.73 minus 1.00 g of nuclei equals 4.73 g, i.e., by returning to the same weight of solution racemic as used for the test: 3.70 g.
Excess enantiomeric: 2.37 g, i.e., 8.6%.
Purity optical: 72.6%.
The weight of antipode obtained and the purity optical are greater by the method AS3PC.

5. Resolution of threonine
This example permits comparison of the results obtained by the method AS3PC with the results of the works of Amiard, G. (Bull. Soc. Chim. (1956) 447) carried out by crystallization preferential with nucleation spontaneous.
a) Characteristics of the product
Capacity rotatory specific, 20° C., c=1 g/100 mL, water:

| λ (nm) | 365 | 589 |
|---|---|---|
| $[\alpha]_{20}$ (°) | −81.0 | −28.1 | b) Resolution by the method AS3PC
Conditions related to equilibria
Solubility in water of mixtures racemic:

| T ° C. | 30.0 | 54.5 |
|---|---|---|
| Solubility (% weight) | 14.5 | 23.1 |

Solubility of the antipode: 9.1% at 30° C., ratio α=1.59.
Coordinates of point L: 23.08% weight; temperature $T_L$: 54.5° C.
Evolution of $T_{HOMO}$ with excess enantiomeric: (mixture racemic/(solvent mixture racemic))=23.08%=constant.

| % Antipode (−) | 0 | 2 | 4 | 6 | 8 |
|---|---|---|---|---|---|
| $T_{HOMO}$ (° C.) | 54.5 | 56 | 61.5 | 65 | 68.5 |

Conditions related to kinetics

Temperature $T_B$: 58° C.

Temperature $T_F$: 31° C.

Kinetics of cooling: T=f(t):

| T (° C.) | 58 | 55 | 51 | 47 | 43 | 39d | 34 | 31 |
|---|---|---|---|---|---|---|---|---|
| t (min) | 0 | 12 | 22 | 30 | 38 | 46 | 54 | 60 |

The duration of the state of supersaturation of the solution L subjected to this kinetics: 80 min.

Duration of crystallization: 60 min.

Conditions initial

Excess enantiomeric initial: 5%.

| Weight solvent (g) | Weight (±) (g) | Weight (+) (g) |
|---|---|---|
| 30.00 | 9.00 | 0.47 |

Results

| No. | Weight antipode pure (g) | % Purity optical | Compensation sol. (±) 23.1% |
|---|---|---|---|
| 1 | 1.02 | (+) 97.5 | 1.432 |
| 2 | 1.20 | (−) 94.0 | 1.769 |
| 3 | 1.46 | (+) 93.0 | 1.663 |
| 4 | 1.65 | (−) 97.5 | 1.443 |
| 5 | 1.60 | (+) 98.3 | 0.552 |
| 6 | 1.64 | (−) 98.5 | 1.687 |
| 7 | 1.72 | (+) 99.1 | 1.650 |
| 8 | 1.70 | (−) 92.4 | 1.800 |
| 9 | 1.66 | (+) 91.8 | 1.842 |
| 10 | 1.69 | (−) 97.8 | — |

Weight average of antipode pure (from manipulation no. 4: 1.665 g.

Excess enantiomeric average 0.833 g, i.e., 8.47%.

Purity optical average: 96.5%.

c) Results obtained by Amiard

Conditions initial

| Weight solvent (g) | Weight (±) (g) | Weight (+) (g) |
|---|---|---|
| 150 | 45 | 5 |

Concentration of mixture racemic: 23.08%.

Excess enantiomeric: 10%.

Temperature $T_D$: 80° C.

Temperature $T_F$: 20° C.

Weight of nuclei: nucleation spontaneous at 30° C. without agitation after a time not specified by the author Time of crystallization: 60 min (by agitating from time to time).

Results

Weight average of antipode pure: 7.80 g, i.e. by returning to the weight of solution racemic used in the test: 1.55 g.

Excess enantiomeric average: 3.9 g, i.e., 8%.

Purity optical: 84.2%

Use of the method AS3PC permitted achievement of a recovery of antipode greater with much more regularity and above all with purity optical distinctly improve.

6. Resolution of 5-methyl-5-phenylhydantoin a) Characteristics of the product

Temperature of melting of the antipode: 242° C.

Temperature of melting of the mixture racemic: 196° C.

Capacity rotatory specific at 20° C., c=1 g/100 mL, ethanol:

| λ (nm) | 589 | 578 | 546 | 436 | 365 |
|---|---|---|---|---|---|
| $[\alpha]_{20}$ (°) | 116 | 122 | 139 | 229 | 433 | b) Resolution by the method AS3PC

Conditions related to equilibria

Solubility of mixtures racemic in 2-methoxyethanol:

| T (° C.) | 20.2 | 30.2 | 34.8 | 38.0 | 41.9 |
|---|---|---|---|---|---|
| Solubility s (±) (% weight) | 18.1 | 20.0 | 21.2 | 21.8 | 22.9 |
| Solubility s (+) (% weight) | 9.8 | 10.9 | 11.5 | | |
| Ratio α | 1.84 | 1.84 | 1.84 | | |

Coordinates of point L: 21.48% weight; temperature $T_L$: 37° C.

Evolution of $T_{HOMO}$ with excess enantiomeric: (mixture racemic/(solvent mixture racemic))=21.48%=constant.

| % Enantiomer | 0 | 2 | 4 | 6 |
|---|---|---|---|---|
| $T_{HOMO}$ (° C.) | 37.0 | 39.8 | 42.7 | 45.5 |

Conditions related to kinetics

Temperature $T_B$: 40° C.

Temperature $T_F$: 20° C.

Kinetics of cooling: T=f(t):

| T (° C.) | 40 | 35 | 30 | 25 | 20 | 20 |
|---|---|---|---|---|---|---|
| t (min) | 0 | 12 | 22 | 30 | 38 | 46 |

The duration of the state of supersaturation of the solution L subjected to this kinetics: greater than 90 minutes for a rate of agitation of 150 rpm.

Duration of crystallization: 60 min.

Conditions initial

Excess enantiomeric initial: 5%.

| Weight solvent (g) | Weight (±) (g) | Weight (+) (g) |
|---|---|---|
| 15.704 | 4.296 | 0.229 |

Duration of plateau at $T_B$: 30 minutes.

Rate of agitation: 100 rpm at the beginning of crystallization, then 150 revolutions at the end.
Results

| No. | Weight antipode pure (g) | % Purity optical | Compensation sol. (±) 23.1% |
|---|---|---|---|
| 1 | 0.560 | (+) 94 | 2.224 |
| 2 | 0.551 | (−) 89 | 1.632 |
| 3 | 0.629 | (+) 92 | 1.174 |
| 4 | 0.561 | (−) 92 | 1.095 |
| 5 | 0.599 | (+) 91 | 0.967 |
| 6 | 0.626 | (−) 92 | 1.034 |
| 7 | 0.510 | (+) 91 | 0.942 |
| 8 | 0.521 | (−) 87 | 1.181 |
| 9 | 0.568 | (+) 89 | |

Weight average of antipode pure: 0.569 g.
Excess enantiomeric average 0.285 g, i.e., 6.2%.
Purity optical average: 91%.

7. Resolution of 5-methyl-5-(4-methylphenyl)hydantoin
a) Characteristics of the product
Temperature of melting of the antipode: 250° C.
Temperature of melting of the mixture racemic: 205° C.
Capacity rotatory specific at 20° C., c=1 g/100 mL, ethanol.

| $\lambda$ (nm) | 589 | 578 | 546 | 436 | 365 |
|---|---|---|---|---|---|
| $[\alpha]_{20}$ (°) | 105 | 110 | 127 | 234 | 418 | b) Resolution by the method AS3PC
Conditions related to equilibria
Solubility of mixtures racemic in 2-methoxyethanol:

| T (° C.) | 15 | 25 | 39 | 45 | 50 |
|---|---|---|---|---|---|
| Solubility s (% weight) | 12.9 | 14.4 | 17.0 | 19.5 | 20.1 |

Solubility of the antipode R: 7.5% at 25° C., ratio $\alpha$=1.92 at 25° C.
Coordinates of point L: 17% weight; temperature $T_L$: 39°C.
Evolution of $T_{HOMO}$ with excess enantiomeric: (mixture racemic/(solvent mixture racemic))=17%=constant.

| % Enantiomer | 0 | 2 | 4 | 6 | 8 |
|---|---|---|---|---|---|
| $T_{HOMO}$ (° C.) | 39 | 41.3 | 43.7 | 46 | 48.3 |

Conditions related to kinetics
Temperature $T_B$: 41° C.
Temperature $T_F$: 14° C.
Kinetics of cooling: T=f(t):

| T (° C.) | 41 | 31 | 31 | 21 | 21 | 14 |
|---|---|---|---|---|---|---|
| t (min) | 0 | 15 | 30 | 45 | 50 | 60 |

The duration of the state of supersaturation of the solution L subjected to this kinetics: 70 minutes for a rate of agitation of 150 rpm.

Duration of crystallization: 60 minutes.
Conditions initial
Excess enantiomeric initial: 7.4%.

| Weight solvent (g) | Weight (±) (g) | Weight (+) (g) |
|---|---|---|
| 27.68 | 5.667 | 0.458 |

Duration of plateau at $T_B$: 30 minutes.
Rate of agitation: 150 rpm at the beginning of crystallization, then 200 revolutions at the end.
Results

| No. | Weight antipode pure (g) | % Purity optical | Compensation sol. (±) 23.1% |
|---|---|---|---|
| 1 | 0.882 | (+) 93 | 1.085 |
| 2 | 0.914 | (−) 91 | 1.170 |
| 3 | 0.860 | (+) 93 | 1.224 |
| 4 | 0.887 | (−) 95 | 1.263 |
| 5 | 0.905 | (+) 96 | 1.100 |
| 6 | 0.929 | (−) 95 | 1.200 |
| 7 | 0.882 | (+) 93 | 1.888 |
| 8 | 1.002 | (−) 99 | 1.209 |
| 9 | 1.064 | (+) 93 | 1.387 |
| 10 | 1.164 | (−) 94 | 1.598 |
| 11 | 1.165 | (+) 90 | 2.356 |
| 12 | 1.071 | (−) 82 | 0.538 |

Weight average of crystals of antipode pure: 0.977 g.
Excess enantiomeric average 0.489 g, i.e., 7.9%.
Purity optical average: 93%.

8. Resolution of 5-ethyl-5-phenylhydantoin
This compound was resolved by Cave et al. (Patent of the U.S. Pat. No. 2,942,004) using the method conventional SIPC in another solvent less appropriate than 2-methoxyethanol.
a) Characteristics of the product
Temperature of melting of the antipode: 240° C.
Temperature of melting of the mixture racemic: 197° C.
Capacity rotatory specific at 20° C., c=1 g/100 mL, ethanol.

| $\lambda$ (nm) | 589 | 578 | 546 | 436 | 365 |
|---|---|---|---|---|---|
| $[\alpha]_{20}$ (°) | 117 | 122 | 141 | 261 | 462 | b) Resolution by the method AS3PC
Conditions related to equilibria
Solubility of mixtures racemic in 2-methoxyethanol:

| T (° C.) | 20 | 30 | 41 | 50 | 60 |
|---|---|---|---|---|---|
| Solubility s (% weight) | 13.6 | 15.6 | 17.0 | 19 | 23.0 |

Solubility of the antipode R: 9.5% at 41° C., ratio $\alpha$=1.8 at 41° C.
Coordinates of point L: 17% weight; temperature $T_L$: 41° C.
Evolution of $T_{HOMO}$ with excess enantiomeric: (mixture racemic/(solvent mixture racemic))=17%=constant.

| % Enantiomer | 0 | 2 | 4 | 6 | 8 |
|---|---|---|---|---|---|
| $T_{HOMO}$ (° C.) | 41 | 43.6 | 46.3 | 48.7 | 51.5 |

Conditions related to kinetics

Temperature $T_B$: 44.5° C.

Temperature $T_F$: 23° C.

Kinetics of cooling: T=f(t):

| T (° C.) | 44.5 | 41 | 39 | 37 | 35 | 33 | 31 | 29 | 27 | 25 | 23 |
|---|---|---|---|---|---|---|---|---|---|---|---|
| t (min) | 0 | 10 | 15 | 20 | 25 | 30 | 35 | 41 | 46 | 51 | 56 |

The duration of the state of supersaturation of the solution L subjected to this kinetics: 70 minutes for a rate of agitation of 275 rpm.

Duration of crystallization: 56 minutes.

Conditions initial

Excess enantiomeric initial: 6.4%.

| Weight solvent (g) | Weight (±) (g) | Weight (+) (g) |
|---|---|---|
| 27.666 | 5.666 | 0.3877 |

Duration of plateau at $T_B$: 30 minutes.

Rate of agitation: 200 rpm at the beginning of crystallization, then 275 revolutions at the end.

Results

| No. | Weight antipode pure (g) | % Purity optical | Compensation sol. (±) 23.1% |
|---|---|---|---|
| 1 | 0.717 | (+) 91 | 0.742 |
| 2 | 0.838 | (−) 80 | 1.765 |
| 3 | 1.002 | (+) 92 | 0.894 |
| 4 | 1.016 | (−) 88 | 1.116 |
| 5 | 1.088 | (+) 92 | 0.806 |
| 6 | 1.161 | (−) 90 | 0.654 |
| 7 | 1.137 | (+) 86 | 1.446 |
| 8 | 1.135 | (−) 85 | 2.440 |
| 9 | 1.179 | (+) 87 | |

Weight average of crystals of antipode pure: 1.030 g

Excess enantiomeric average 0.515 g, i.e., 8.5%.

Purity optical average: 88%.

9. Resolution of 5-methyl-5-(4-chlorophenyl)hydantoin a) Characteristics of the product Temperature of melting of the antipode: 305° C.

Temperature of melting of the mixture racemic: 263° C.

Capacity rotatory specific at 20° C., c=1 g/100 mL, ethanol.

| λ (nm) | 578 | 546 | 436 | 365 |
|---|---|---|---|---|
| $[\alpha]_{20}$ (°) | 112 | 130 | 241 | 434 | b) Resolution by the method AS3PC

Conditions related to equilibria

Solubility of mixtures racemic in 2-methoxyethanol:

| T (° C.) | 20 | 40 | 50 | 60 |
|---|---|---|---|---|
| Solubility s (% weight) | 3.5 | 4.7 | 5.6 | 6.5 |

Solubility of the antipode R: 1.72% at 20° C., ratio α=2.03 at 20° C.

Coordinates of point L: 6.05% weight; temperature $T_L$: 55° C.

Evolution of $T_{HOMO}$ with excess enantiomeric: (mixture racemic/(solvent mixture racemic))=6.05%=constant.

| % Enantiomer | 0 | 4 | 8 |
|---|---|---|---|
| $T_{HOMO}$ (° C.) | 55 | 60 | 65 |

Conditions related to kinetics

Temperature TB: 57° C.

Temperature TF: 27° C.

Kinetics of cooling: T=f(t):

| T (° C.) | 57 | 35 | 27 | 27 |
|---|---|---|---|---|
| t (min) | 0 | 32 | 52 | 115 |

The duration of the state of supersaturation of the solution L subjected to this kinetics: 120 minutes for a rate of agitation of 150 rpm.

Duration of crystallization: 115 minutes.

Conditions initial

Excess enantiomeric initial: 6.52%.

| Weight solvent (g) | Weight (±) (g) | Weight (+) (g) |
|---|---|---|
| 95.7 | 6.166 | 0.430 |

Duration of plateau at $T_B$: 60 minutes.

Rate of agitation: 200 rpm.

Results

| No. | Weight antipode pure (g) | % Purity optical | Compensation sol. (±) 23.1% |
|---|---|---|---|
| 1 | 0.889 | (+) 90.7 | 2.010 |
| 2 | 0.931 | (−) 91.8 | 1.826 |
| 3 | 0.661 | (+) 91.1 | 1.992 |
| 4 | 1.083 | (−) 89.0 | 2.258 |
| 5 | 1.381 | (+) 92.9 | 5.559 |
| 6 | 1.330 | (−) 92.4 | 2.535 |
| 7 | 1.397 | (+) 91.9 | 2.195 |
| 8 | 1.410 | (−) 93.9 | |

Weight average of crystals of antipode pure: 1.13 g.

Excess enantiomeric average 0.568 g, i.e., 8.6%.

Purity optical average: 91.7%

10. Resolution of threitol a) Characteristics of the product

Temperature of melting of the antipode: 92° C.

Temperature of melting of the mixture racemic: 70° C.

Capacity rotatory specific at 20° C., c=1 g/100 mL, ethanol.

| λ (nm) | 589 | 578 | 546 | 436 | 365 |
|---|---|---|---|---|---|
| $[\alpha]_{20}$ (°) | 14.2 | 14.8 | 16.8 | 29.3 | 47.4 | b) Resolution by the method AS3PC

Conditions related to equilibria

Solubility of mixtures racemic in the mixture ethanol 95%/water 5%:

| T (° C.) | 21.1 | 23.1 | 25.1 | 26.7 | 27.0 | 30.9 | 31.4 | 34.3 |
|---|---|---|---|---|---|---|---|---|
| Solubility s (% weight) | 9.3 | 10.2 | 11.3 | 12.2 | 12.5 | 15.9 | 16.6 | 20.1 |

Solubility of the antipode R: 4.4% at 27° C., ratio α=2.8 at 27° C.

Coordinates of point L: 12.5% weight; temperature $T_L$: 27° C.

Evolution of $T_{HOMO}$ with excess enantiomeric: (mixture racemic/(solvent mixture racemic))=12.5%=constant.

| % Enantiomer | 0 | 2 | 4.12 | 5.85 | 7.90 |
|---|---|---|---|---|---|
| $T_{HOMO}$ (° C.) | 27.0 | 27.8 | 28.6 | 29.3 | 29.8 |

Conditions related to kinetics

Temperature $T_B$: 27.5° C.

Temperature $T_F$: 19.4° C.

Kinetics of cooling: T=f(t):

| T (° C.) | 27.5 | 26.8 | 26.8 | 23.3 | 23.3 | 19.4 | 19.4 |
|---|---|---|---|---|---|---|---|
| t (min) | 0 | 1.5 | 5 | 11 | 15 | 22 | 60 |

The duration of the state of supersaturation of the solution L subjected to this kinetics: 60 minutes for a rate of agitation of 100 rpm.

Duration of crystallization: 60 minutes.

Conditions initial

Excess enantiomeric initial: 6%.

| Weight solvent (g) | Weight (±) (g) | Weight (+) (g) |
|---|---|---|
| 87.50 | 12.50 | 0.800 |

Duration of plateau at $T_B$: 20 minutes.

Rate of agitation: 100 rpm at the beginning of crystallization, then 200 revolutions at the end.

Results

The filtration is carried out on a glass sintered no. 2; the crystals are washed with diisopropyl ether.

| No. | Weight antipode pure (g) | % Purity optical | Compensation sol. (±) 23.1% |
|---|---|---|---|
| 1 | 1.637 | (+) 89 | 2.107 |
| 2 | 1.740 | (−) 96.2 | 2.260 |
| 3 | 1.916 | (+) 96.7 | 2.364 |
| 4 | 2.040 | (−) 96 | 2.622 |
| 5 | 1.703 | (+) 93.3 | 2.353 |
| 6 | 1.856 | (−) 96.2 | 2.387 |
| 7 | 1.932 | (+) 96 | 2.403 |
| 8 | 1.649 | (−) 93.3 | 2.39 |
| 9 | 1.615 | (+) 93.2 | 2.17 |
| 10 | 1.721 | (−) 92.4 | 2.39 |

Weight average of crystals of antipode pure: 1.780 g.

Excess enantiomeric average 0.890 g, i.e., 6.7%.

Purity optical average: 94.2%.

We claim:

1. A method for the alternate, batch-wise resolution of two optical enantiomers by preferential crystallization which comprises:

a) preparing a racemic mixture of crystals in conglomerate form, of the first enantiomer and a solvent, the figurative point E of which, defined by the variables concentrations and temperature Tg, is situated in the two-phase domain of the first enantiomer in excess, with its saturated solution;

b) cooling the two phase mixture of step (a) in accordance with a temperature kinetic schedule, so that the mother liquor retains a slight supersaturation that promotes the growth of the first enantiomer present in crystal form, while preventing the spontaneous nucleation of the second enantiomer present in the solution;

c) using during the entire duration of the crystalline growth of step (b) an agitation rate that increases slightly as a function of time such that this rate is at all times sufficiently slow to favor the growth of the first enantiomer while avoiding the generation of excessively high striction forces that would induce uncontrolled nucleation, and sufficiently rapid so as to create a homogeneous suspension and rapid renewal of the mother liquor around each crystallite of the first enantiomer;

d) harvesting the crystals of the first enantiomer:

e) adding the racemic mixture of crystals in conglomerate form to the mother liquors resulting from the harvest of the crystals of the first enantiomer performed in step (d) and bringing the mixture to a temperature threshold $T_B$ for the time required to with E in relation to the plane of the racemic-mixtures of the solvent system enantiomer (−), enantiomer (+), with said point E' being situated in the two-phase domain of the second enantiomer in excess and in thermodynamic equilibrium with its saturated solution;

f) cooling in accordance with the temperature kinetic schedule the two-phase mixture of step (e) containing the second enantiomer, so that the mother liquors retain a slight supersaturation during the crystallization that promotes the growth of the second enantiomer present in the crystal form while preventing the spontaneous nucleation of the first enantiomer present in the solution;

g) using during the entire duration of the crystalline growth of step (f) an agitation rate that increases slightly as a function of time such that this rate is at all times sufficiently slow to favor the growth of the second enantiomer while avoiding the generation of excessively high striction forces that would induce uncontrolled nucleation, and sufficiently rapid so as to create a homogeneous suspension and rapid renewal of the mother liquor around each crystallite;

h) harvesting the crystals of the second enantiomer;

i) adding to the racemic mixture crystals in conglomerate form the mother liquors resulting from the harvest of the crystals of the second enantiomer formed in step (h) and bringing the mixture to a temperature threshold $T_B$ for the time required to reach the thermodynamic equilibrium so that the figurative point E' is symmetrical with E in relation to the plane of the racemic mixtures of the solvent system, whereby the results a mixture which is identical to the initial mixture of (a); and j) repeating steps (a), (b), (c), (d), (e), (f), (g), (h) and (i) so as to obtain successively the one and then the other of the two enantiomers.

2. The method in accordance with claim 1, wherein in step (a), the selection of the solvent(s) and of the operating temperature range are defined in as to have simultaneously:

enantiomers that form a conglomerate and the possible racemate thereof which is metastable in the operating temperature range;

liquors that are sufficiently concentrated but of low viscosity and low vapor pressure;

a lack of solvolysis and racemization; and a stability of the solvates, if present, in equilibrium wherein said solutes involve resolvable enantiomers.

3. The method in accordance with claim 1, wherein in steps (a) and (e), the temperature $T_B$ is maintained higher than the temperature $T_L$ of homogenization of the racemic mixture contained in the initial suspension, and that, based on the curve of variation of $T_{HOMO}$ as a function of the enantiomeric excess and for a constant concentration in racemic mixture $X_L$, the temperature $T_B$ is defined so that the mass of fine crystals of the first enantiomer of steps (a) and (i) and of the second enantiomer of step (e), in equilibrium with the respective saturated solution, represents at maximum 50% of the anticipated harvest.

4. The method of claim 1, wherein the cooling in one of the preceding claims in steps (b) and (f) in accordance with the temperature kinetic schedule applied to temperature $T_B$ to $T_F$, adapted to the experimental set-up, is defined:

to obtain a slight supersaturation during the entire duration of the crystallization of the enantiomer present in crystal form at the beginning of each cycle, with the slight supersaturation inducing a gentle growth and secondary nucleation;

to reach a $T_F$ the maximum of supersaturation of the other enantiomer without primary nucleation;

to obtain a crystal harvest in steps (d) and (h) which, after addition of racemic mixture and compensation to steps (e) and (i), makes possible the cyclicity of the operations.

5. The method in accordance with claim 4, wherein the cooling in accordance with the temperature kinetic schedule is determined for its part from $T_L$ to $T_F$ by cooling the solution of concentration $X_L$ from $T_L+1°$ C. to $T_F$, with $T_F$ being lower than $T_L-(T_{HOMO}-T_L)$, so as to obtain a stable saturated solution without primary nucleation while still permitting a soluble harvesting of the initial enantiomeric excess, and in that said cooling in accordance with the temperature kinetic schedule is determined for its part from $T_B$ to $T_L$ by extrapolation from this same schedule as determined from $T_L+1°$ C. to $T_F$.

6. The method in accordance with claim 1, wherein in steps (b) and (f), the thermicity accompanying the deposit of the first enantiomer and of the second enantiomer is integrated into the temperature kinetic schedule.

7. The method of claim 1, wherein in steps (e) and (i), solvent compensations are implemented.

8. The method of claim 1, wherein in steps (a), (e) and (i), the fine crystals of the racemic mixture in conglomerate form which are added, have been subjected prior to their introduction to a pretreatment accelerating the dissolution step, such as grinding and sifting, ultrasound treatment and partial lyophilzation.

9. The method of claim 1, wherein in steps (a), (e) and (i), the agitation rate is increased.

10. The method of claim 1, for the resolution of two optical enantiomers optical of tartrate of sodium and ammonium tartrate tetrahydrated which comprises:

in step (a), the mixture initial comprises the following:
solvent: 5.67 g water,
racemic mixture: 4.83 g
enantiomer (+): 0.23 g, and
$T_L=16.3°$ C.,
$T_B=17.3°$ C.,
duration of step at $T_B=40$ min
in step (b), the cooling temperature kinetic schedule from $T_B$ to $T_F$ is given by the values of the temperatures as a function of time as shown below:

| T (° C.) | 17.3 | 17.0 | 16.5 | 15.4 | 14.0 | 13.0 | 12.1 | 12.0 | 12.0 |
|---|---|---|---|---|---|---|---|---|---|
| t (min) | 0 | 3 | 5 | 8 | 12.5 | 16 | 20 | 25 | 30 | in step (c), the agitation is 150 rpm at the beginning and 170 rpm at the end of crystallization, in step (d), the crystals are harvested on glass frit no. 2, in step (e), there is added a racemic mixture that has been ground and screened to 250μ, and in addition to the compensation for losses, there is added ammonia so as to maintain a slight excess thereof and:

$T_L=16.3°$ C.,
$T_B=17.3°$ C.,
duration of the step at $T_B=40$ min
in step (f), the cooling temperature kinetic schedule $T_b$ to $T_F$ is given by the values of temperatures as a function of time as shown below:

| T (° C.) | 17.3 | 17.0 | 16.5 | 15.4 | 14.0 | 13.0 | 12.1 | 12.0 | 12.0 |
|---|---|---|---|---|---|---|---|---|---|
| t (min) | 0 | 3 | 5 | 8 | 12.5 | 16 | 0 | 25 | 30 | in step (g), the agitation rate is 150 rpm at the beginning and 170 rpm at the end of crystallization, in step (h), the crystals are harvested on glass frit no. 2, in step (i), there is added a racemic mixture that has been ground and sifted to 250μ, and in addition to the compensations for there is added ammonia so as to maintain a slight excess thereof.

11. The method of claim 1 for the resolution of the two optical enantiomers of 5-methyl-5phenylhydantoin which comprises:

in step (a), the mixture initial comprises the following:
solvent: 15.704 g of 2-methoxyethanol,
racemic mixture: 4.296 g,
enantiomer (+): 0.229 g and
$T_L$=37° C.,
$T_B$=40° C.,
duration of the step $T_B$=30 min
in step (b), the cooling temperature kinetic schedule from $T_B$ to $T_F$ is given by the values of the temperatures as a function of time as shown below:

| T (° C.) | 40 | 35 | 30 | 25 | 20 | 20 |
|---|---|---|---|---|---|---|
| t (min) | 0 | 12 | 22 | 30 | 38 | 46 | in step (c), the agitation rate is 100 rpm at the beginning and 150 rpm at the end of crystallization,
in step (d), the crystals are harvested on glass frit no. 3,
in step (e), there is added a racemic mixture and there are implemented the usual compensations, and:
$T_L$=37° C.,
$T_B$=40° C.,
duration of the step at $T_B$=30 min
in step (f), the cooling temperature kinetic schedule from $T_B$ to $T_F$ is given by the values of temperatures as a function of time as shown below:

| T (° C.) | 40 | 35 | 30 | 25 | 20 | 20 |
|---|---|---|---|---|---|---|
| t (min) | 0 | 12 | 22 | 30 | 38 | 46 | in step (g), the agitation rate is 100 rpm at the beginning and 150 rpm at the end of crystallization,
in step (h), the crystals are harvested on glass frit no. 3,
in step (i), there is the added racemic mixture and there are implemented the necessary compensations.

12. The method for the resolution of the two optical enantiomers of 5-methyl-5-(4-methyl phenyl)-hydantoin which comprises:

in step (a), the initial mixture which comprises the following:
solvent: 27.68 g of 2-methoxy-ethanol,
racemic mixture: 5.667 g,
enantiomer (+): 0.458 g and
$T_L$=39° C.,
$T_B$=41 ° C.,
duration of the step at $T_B$=30 minutes;
in step (b), the cooling temperature kinetic schedule from $T_B$ to $T_F$ is given by the values of the temperatures as a function of time as shown below:

| T (° C.) | 41 | 31 | 31 | 21 | 21 | 14 |
|---|---|---|---|---|---|---|
| t (min) | 0 | 15 | 30 | 45 | 50 | 60 | in step (c), the agitation rate is 150 rpm at the beginning and 200 rpm at the end of crystallization,
in step (d), the crystals are harvested on glass frit no. 3,
in step (e), there is added racemic mixture and there are implemented the usual compensations and:
$T_L$=39° C.,
$T_B$=41 ° C.,
duration of plateau at $T_B$=30 min
in step (f), the cooling temperature kinetic schedule from $T_B$ to $T_F$ is given by the values of temperatures as a function of time as shown below:

| T (° C.) | 41 | 31 | 31 | 21 | 21 | 14 |
|---|---|---|---|---|---|---|
| t (min) | 0 | 15 | 30 | 45 | 50 | 60 | in step (g), the agitation rate is 150 rpm at the beginning and 200 rpm at the end of crystallization,
in step (h), the recovery of crystals is carried out on glass sintered no. 3,
in step (i), there is added the racemic mixture and there are implemented the necessary compensations.

13. The method of claim 1 for the resolution of the two optical enantiomers of 5-ethyl-5-phenyl-hydantoin which comprises:

in step (a), the initial mixture is the following:
solvent: 27.666 g of 2-methoxy-ethanol,
racemic mixture: 5.666 g,
enantiomer (+): 0.3877 g and
$T_L$=41° C.,
$T_B$=44.5° C.,
duration of step at $T_B$=30 min;
in step (b), the cooling temperature kinetic schedule from $T_B$ to $T_F$ is given by the values of the temperatures as a function of time as shown below:

| T (° C.) | 44.5 | 41 | 39 | 37 | 35 | 33 | 31 | 29 | 27 | 25 | 23 |
|---|---|---|---|---|---|---|---|---|---|---|---|
| t (min) | 0 | 10 | 15 | 20 | 25 | 30 | 35 | 41 | 46 | 51 | 56 | in step (c), the agitation rate is 200 rpm at the beginning and 275 rpm at the end of crystallization,
in step (d), the crystals are harvested on glass frit no. 3,
in step (e), there is added a racemic mixture, there is implemented the usual compensations and:
$T_L$=41° C.,
$T_B$=44.50° C.,
duration of step at $T_B$=30 min
in step (f), the cooling temperature kinetic schedule from $T_B$ to $T_F$ is given by the values of temperatures as a function of time as shown below:

| T (° C.) | 44.5 | 41 | 39 | 37 | 35 | 33 | 31 | 29 | 27 | 25 | 23 |
|---|---|---|---|---|---|---|---|---|---|---|---|
| t (min) | 0 | 10 | 15 | 20 | 25 | 30 | 35 | 41 | 46 | 51 | 56 | in step (g), the agitation rate is 200 rpm at the beginning and 275 rpm at the end of crystallization,
in step (h), the crystals are harvested on glass frit no. 3,
in step (i), there is added the racemic mixture and there are implemented the necessary compensations.

14. The method for the resolution of the two optical enantiomers of 5-methyl-5-(4-chlorophenyl)-hydantoin according to claim 1 which comprises:
in step (a), the initial mixture is the following:

solvent: 94.7 g of 2-methoxy-ethanol,
racemic mixture: 6.166 g,
enantiomer (+): 0.430 g and
$T_L$=55° C.,
$T_B$=57° C.,
duration of the step at $T_B$=60 min;
in step (b), the cooling schedule from $T_B$ to $T_F$ is given by the values of the temperatures as a function of time as shown below:

| T (° C.) | 57 | 35 | 27 | 27 |
|---|---|---|---|---|
| t (min) | 0 | 32 | 52 | 115 | in step (c), the agitation rate is 150 rpm at the beginning and 200 rpm at the end of crystallization,
in step (d), the crystals are harvested on glass frit no. 3,
in step (e), there is added the racemic mixture, and there are implemented the usual compensations, and:
$T_L$=55° C.,
$T_B$=57° C.,
duration of step at $T_B$=60 min
in step (f), the cooling temperature kinetic schedule from $T_B$ to $T_F$ is given by the values of temperatures as a function of time as shown below:

| T (° C.) | 57 | 35 | 27 | 27 |
|---|---|---|---|---|
| t (min) | 0 | 32 | 52 | 115 | in step (g), the agitation rate is 200 rpm at the beginning and 275 rpm at the end of crystallization,
in step (h), the crystals are harvested on glass frit no. 3,
in step (i), there is added the racemic mixture and there are implemented the necessary compensations.

15. The method for the resolution of the two optical enantiomers of threitol accordance to claim 1 which comprises:
in step (a), the initial mixture is the following:
solvent: 87.5 g of mixture ethanol 95%/water 5%,
racemic mixture: 12.50 g,
enantiomer (+): 0.800 g and
$T_L$=27° C.,
$T_B$=27° C.,
duration of step at $T_B$=20 min;
in step (b), the cooling temperature kinetic schedule from $T_B$ to $T_F$ is given by the values of the temperatures as a function of time as shown below:

| T (° C.) | 27.5 | 26.8 | 26.8 | 23.3 | 23.3 | 19.4 | 19.4 |
|---|---|---|---|---|---|---|---|
| t (min) | 0 | 1.5 | 5 | 11 | 15 | 22 | 60 | in step (c), the agitation rate is 100 rpm at the beginning and 120 rpm at the end of crystallization,
in step (d), the crystals are harvested on glass frit no. 2 followed by a washing with diisopropyl ether;
in step (e), there is added the racemic mixture, and there is implemented the usual compensations, and:
$T_L$=27° C.,
$T_B$=27.5° C.,
duration of step at $T_B$=20 min
in step (f), the cooling temperature kinetic schedule from $T_B$ to $T_F$ is given by the values of temperatures as a function of time as shown below:

| T (° C.) | 27.5 | 26.8 | 26.8 | 23.3 | 23.3 | 19.4 | 19.4 |
|---|---|---|---|---|---|---|---|
| t (min) | 0 | 1.5 | 5 | 11 | 15 | 22 | 60 | in step (g), the agitation rate is 100 rpm at the beginning and 120 rpm at the end of crystallization,
in step (h), the crystals are harvested on glass frit no. 2 followed by washing with diisopropyl ether,
in step (i), there is added the racemic mixture and there are implemented necessary compensations.

16. The method of claim 3, wherein respective saturated solution represent about 25 to 40% of the anticipated harvest.

17. The method of claim 1, wherein in step (e) the mass of five crystals of the second enantiomer in equilibrium with the saturated solution represents not more than 50%^ of the anticipated harvest.

18. The method of claim 16, wherein the respective saturated solution represents about 25 to 40% of the anticipated harvest.

19. The method of claim 1, wherein in step (e) heating the mixture $T_B$ where all the antipode is dissolved.

* * * * *